(12) United States Patent
Tegels et al.

(10) Patent No.: US 11,571,297 B2
(45) Date of Patent: Feb. 7, 2023

(54) APPARATUS AND METHODS FOR DELIVERY OF A PROSTHETIC VALVE WITHIN AN EXISTING IMPLANTED PROSTHETIC VALVE

(71) Applicant: Tendyne Holdings, Inc., St. Paul, MN (US)

(72) Inventors: Zachary J. Tegels, Minneapolis, MN (US); Michael J. Urick, Chaska, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 241 days.

(21) Appl. No.: 16/914,944

(22) Filed: Jun. 29, 2020

(65) Prior Publication Data

US 2021/0022855 A1    Jan. 28, 2021

Related U.S. Application Data

(60) Provisional application No. 62/877,882, filed on Jul. 24, 2019.

(51) Int. Cl.
A61F 2/24    (2006.01)
A61M 25/00    (2006.01)

(52) U.S. Cl.
CPC .......... *A61F 2/2418* (2013.01); *A61F 2/2409* (2013.01); *A61F 2/2433* (2013.01);
(Continued)

(58) Field of Classification Search
CPC .... A61F 2/2418; A61F 2/2409; A61F 2/2433; A61F 2220/0016
See application file for complete search history.

(56) References Cited

U.S. PATENT DOCUMENTS

| | | | |
|---|---|---|---|
| 2009/0132035 A1* | 5/2009 | Roth | A61F 2/2415 623/2.14 |
| 2012/0209375 A1 | 8/2012 | Madrid et al. | |

(Continued)

FOREIGN PATENT DOCUMENTS

| | | |
|---|---|---|
| EP | 3417903 A1 | 12/2018 |
| WO | 0160443 A1 | 8/2001 |

(Continued)

OTHER PUBLICATIONS

Partial International Search Report including provisional opinion for Application No. PCT/US2020/040071, dated Aug. 20, 2020, pp. 1-11.

(Continued)

*Primary Examiner* — Suba Ganesan
(74) *Attorney, Agent, or Firm* — Wei & Sleman LLP

(57) ABSTRACT

Apparatus and methods are described herein for a secondary valve apparatus that can be deployed within an existing implanted prosthetic heart valve. In some embodiments, a secondary prosthetic heart valve apparatus is implanted in series with an existing deteriorating implanted prosthetic valve. The secondary valve apparatus can restore proper valve function without disruption to the failing previously implanted valve. In some embodiments, the secondary valve apparatus can be positioned on an atrial portion of the existing valve, and be delivered transseptally. In other embodiments, the secondary valve apparatus can be positioned at a ventricular portion of the existing valve and delivered transapically. Devices and methods to prepare the existing valve to receive a secondary valve apparatus are also described herein. In some embodiments, a balloon expansion device can be used to expand an inner diameter of the existing valve to provide space for the secondary valve to be disposed.

16 Claims, 34 Drawing Sheets

(52) U.S. Cl.
CPC .... *A61F 2/2457* (2013.01); *A61F 2220/0016* (2013.01); *A61M 25/0021* (2013.01); *A61M 2025/0042* (2013.01)

(56) References Cited

U.S. PATENT DOCUMENTS

| | | | |
|---|---|---|---|
| 2012/0283820 A1* | 11/2012 | Tseng | A61F 2/2418 623/1.23 |
| 2017/0079790 A1 | 3/2017 | Vidlund et al. | |
| 2017/0312078 A1* | 11/2017 | Krivoruchko | A61F 2/2457 |
| 2021/0338419 A1* | 11/2021 | Gifford, III | A61F 2/2409 |

FOREIGN PATENT DOCUMENTS

| | | |
|---|---|---|
| WO | 2014063039 A1 | 4/2014 |
| WO | 2015120122 A2 | 8/2015 |
| WO | 2016112085 A2 | 7/2016 |

OTHER PUBLICATIONS

International Search Report including Written Opinion for Application No. PCT/US2020/040071, dated Nov. 3, 2020, pp. 1-18.

* cited by examiner

APPARATUS AND METHODS FOR DELIVERY OF A PROSTHETIC VALVE WITHIN AN EXISTING IMPLANTED PROSTHETIC VALVE

CROSS-REFERENCE TO RELATED APPLICATIONS

This application claims the benefit of the filing date of U.S. Provisional Patent Application No. 62/877,882, filed Jul. 24, 2019, the disclosure of which is hereby incorporated by reference herein.

BACKGROUND OF THE DISCLOSURE

Embodiments are described herein that relate to devices and methods for use in the delivery and deployment of prosthetic heart valves, and particularly to devices and methods for delivery of a prosthetic heart valve within an existing implanted prosthetic heart valve.

Prosthetic heart valves can pose particular challenges for delivery and deployment within a heart. Valvular heart disease, and specifically, aortic and mitral valve disease is a significant health issue in the United States (US); annually approximately 90,000 valve replacements are conducted in the US. Traditional valve replacement surgery involving the orthotopic replacement of a heart valve is considered an "open heart" surgical procedure. Briefly, the procedure necessitates surgical opening of the thorax, the initiation of extra-corporeal circulation with a heart-lung machine, stopping and opening the heart, excision and replacement of the diseased valve, and re-starting of the heart. While valve replacement surgery typically carries a 1-4% mortality risk in otherwise healthy persons, a significantly higher morbidity is associated to the procedure largely due to the necessity for extra-corporeal circulation. Further, open heart surgery is often poorly tolerated in elderly patients. Thus elimination of the extra-corporeal component of the procedure could result in reduction in morbidities and cost of valve replacement therapies could be significantly reduced.

While replacement of the aortic valve in a transcatheter manner is the subject of intense investigation, less attention has been focused on the mitral valve. This is in part reflective of the greater level of complexity associated to the native mitral valve apparatus, and thus, a greater level of difficulty with regards to inserting and anchoring the replacement prosthesis. A need exists for delivery devices and methods for transcatheter mitral valve replacements.

Some known delivery methods include delivering a prosthetic mitral valve through an apical puncture site. In such a procedure, the valve is placed in a compressed configuration within a lumen of a delivery catheter of, for example, 34-36 French (Fr) (i.e., an outer diameter of about 11-12 mm). Delivery of a prosthetic valve to the atrium of the heart can be accomplished, for example, via a transfemoral approach, transatrially directly into the left atrium of the heart, transapically via the ventricle, or via a jugular approach. After the prosthetic heart valve has been deployed, various known anchoring techniques have been used. For example, some prosthetic heart valves are anchored within the heart using anchoring mechanisms attached to the valve, such as barbs, or other features that can engage surrounding tissue in the heart and maintain the prosthetic valve in a desired position within the heart. Some known anchoring techniques include the use of an anchoring tether that is attached to the valve and anchored to a location on the heart such as an interior or exterior wall of the heart.

In addition, some prosthetic heart valves can be prone to wear over time. Valve function can then be slowly compromised as this occurs, and symptoms may recur. It is therefore desirable to be able to implant another prosthetic valve within the failing implanted valve. Often, however, the prosthetic valve construction may include an inner valve frame with a relatively small diameter, as is the case with many replacement prosthetic mitral valves, which can be too small to easily receive a new prosthetic valve therein. This may be particularly true in the case of transcatheter valves, where the device profile is reduced.

Thus, a need exists for improved devices and techniques for deploying and implanting a prosthetic heart valve apparatus or a portion of a prosthetic heart valve apparatus within various types of existing implanted prosthetic valves.

BRIEF SUMMARY

According to one aspect of the disclosure, apparatus and methods are described herein for a secondary valve apparatus that can be deployed within an existing implanted prosthetic heart valve, such as prosthetic mitral valves. In some embodiments, a secondary prosthetic heart valve apparatus is implanted in series with (or offset in relation to) an existing deteriorating implanted prosthetic valve. The secondary valve apparatus can restore proper valve function without disruption to the failing previously implanted valve. In some embodiments, the secondary valve apparatus can be positioned on an atrial portion of the existing valve, and be delivered transseptally (although other delivery routes may be suitable). In other embodiments, the secondary valve apparatus can be positioned at a ventricular portion of the existing valve and delivered transapically (although other delivery routes may be suitable). Devices and methods to prepare the existing valve to receive a secondary valve apparatus are also described herein. In some embodiments, a balloon expansion device can be used to expand an inner diameter of the existing valve to provide space for the secondary valve to be disposed.

According to another aspect of the disclosure, a method of implanting a secondary prosthetic heart valve includes delivering the secondary prosthetic heart valve to a vicinity of a native valve annulus, the native valve annulus having a primary prosthetic heart valve implanted therein, the primary prosthetic heart valve including a primary frame and a set of primary prosthetic leaflets, the secondary prosthetic heart valve being received within a delivery device in a collapsed condition during the delivering. The secondary prosthetic heart valve may be released from the delivery device to allow the secondary prosthetic heart valve to transition to an expanded condition. The secondary prosthetic heart valve may be coupled to the primary prosthetic heart valve so that secondary prosthetic leaflets of the secondary prosthetic heart valve are positioned in series with (or offset in relation to) the primary prosthetic leaflets of the primary prosthetic heart valve, such that the secondary prosthetic leaflets are positioned a spaced distance from the primary prosthetic leaflets in a direction of blood flow through the primary prosthetic heart valve.

According to a further aspect of the disclosure, a method of implanting a secondary prosthetic heart valve in a heart of a patient includes delivering the secondary prosthetic heart valve to a vicinity of a native valve annulus, the native valve annulus having a primary prosthetic heart valve implanted therein, the primary prosthetic heart valve including a primary outer frame engaged to the native valve annulus, a primary inner frame, a set of primary prosthetic leaflets coupled to the primary inner frame, and a tether having a first end coupled to the primary inner frame and a second end coupled to an anchor that is engaged to a surface of the heart, the secondary prosthetic heart valve being received within a delivery device in a collapsed condition during the delivering. The secondary prosthetic heart valve may be released from the delivery device to allow the secondary prosthetic heart valve to transition to an expanded condition. The secondary prosthetic heart valve may be coupled to the primary prosthetic heart valve so that secondary prosthetic leaflets of the secondary prosthetic heart valve are positioned radially inward of the primary prosthetic leaflets of the primary prosthetic heart valve.

According to still another aspect of the disclosure, a balloon expansion device for expanding a portion of a prosthetic heart valve includes a delivery catheter having a distal end extending along a center longitudinal axis. A plurality of balloons may be at least partially received within the delivery catheter, each of the plurality of balloons having a distal tip portion, a proximal portion, and a guidewire lumen extending to the distal tip portion for receiving a guidewire slidably therethrough, each of the guidewire lumens being radially offset from the center longitudinal axis of the delivery catheter. The plurality of balloons may be configured to be operably coupled to an expansion medium such that a volume of the expansion medium can be communicated to the plurality of balloons to expand the plurality of balloons.

According to still a further aspect of the disclosure, a balloon expansion device for expanding a portion of a prosthetic heart valve includes a delivery catheter. A single balloon may be at least partially received within the delivery catheter, the balloon having a distal tip portion, a proximal portion, a center portion between the proximal portion and the distal portion, and a guidewire lumen extending within the distal tip portion for receiving a guidewire slidably therethrough. The guidewire lumen and the distal tip portion may be radially offset from a longitudinal centerline of the center portion of the balloon. The balloon may be configured to be operably coupled to an expansion medium such that a volume of the expansion medium can be communicated to the balloon to expand the balloon.

According to another aspect of the disclosure, a prosthetic heart valve includes a collapsible and expandable frame including an inner frame and an outer frame positioned radially outward of the inner frame. A plurality of prosthetic leaflets may be coupled to the inner frame. A tether may have a first end configured to couple to the collapsible and expandable frame, and a second end opposite the first end. An anchor member may be coupled to the second end of the tether. The tether may include a tether lumen extending therethrough, and a microcatheter positioned within the tether lumen, the microcatheter including a microcatheter lumen extending therethrough, the microcatheter being more rigid than the tether.

DETAILED DESCRIPTION

Figure 1:
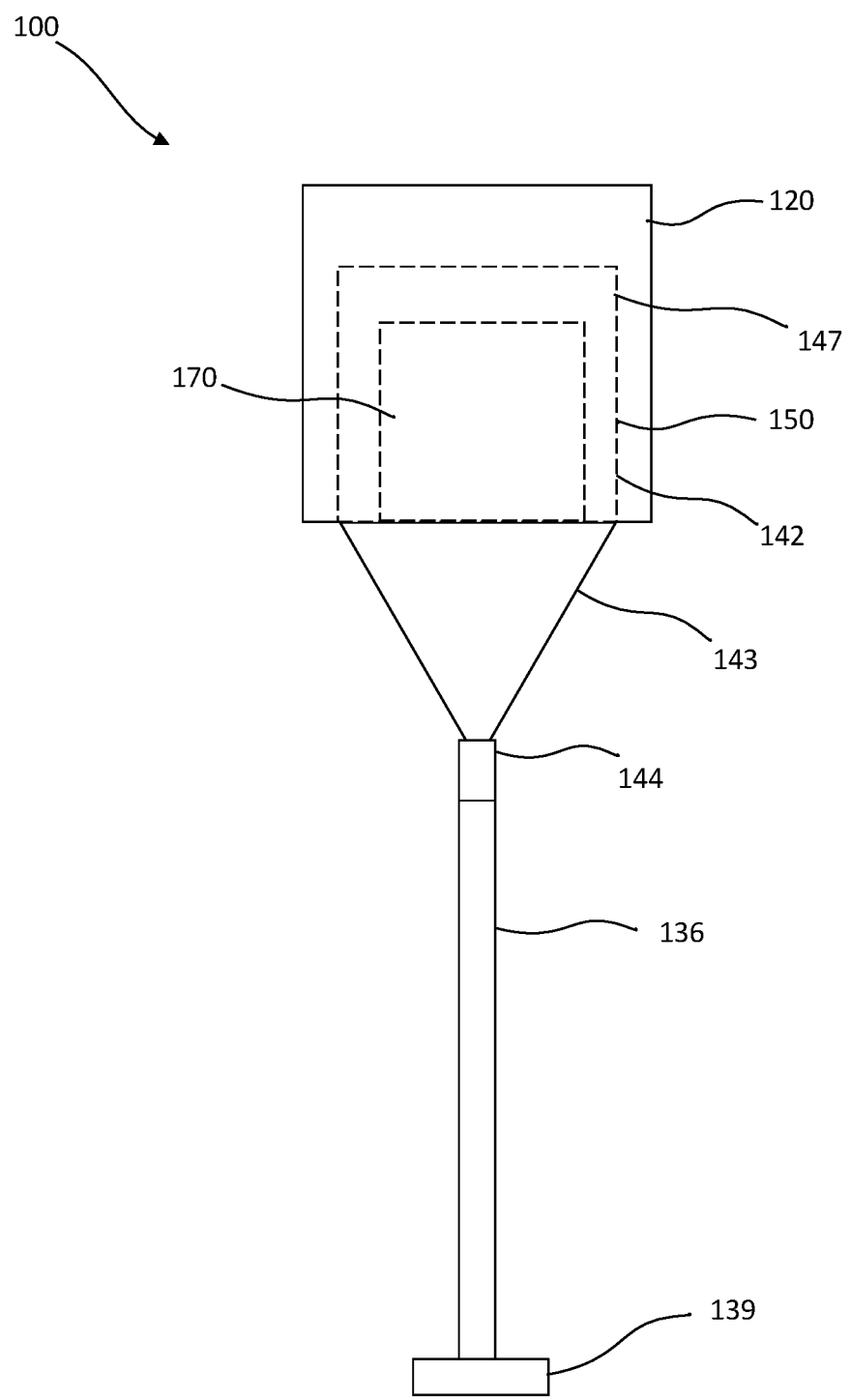
FIG. 1 is a schematic illustration of a prosthetic heart valve, according to an embodiment.

Apparatus and methods are described herein for prosthetic heart valves, such as prosthetic mitral valves, and devices and methods for use in the delivery and deployment of a prosthetic heart valve apparatus within an existing implanted prosthetic heart valve. In some embodiments described herein, a secondary prosthetic heart valve apparatus is implanted in series with (or offset in relation to) an existing deteriorating implanted prosthetic valve. The secondary valve apparatus can restore proper valve function without disruption to the failing previously implanted valve. The secondary valve apparatus could function to stop only the regurgitant blood flow, and would therefore have improved longevity as compared to a stand-alone valve which must withstand the full pressure and volume changes during the cardiac cycle. In the case of a prosthetic mitral valve, in some embodiments, the secondary valve apparatus can be positioned just atrial to the previously implanted valve, and delivered in a transseptal manner. In other embodiments, the secondary valve can be positioned at the ventricular aspect and delivered in a transapical manner.

In some cases, where leaflet deterioration of the implanted prosthetic valve is observed, the inner frame portion of the valve can be modified in-vivo using an expansion device, such as, for example, a balloon catheter and in some embodiments a balloon catheter with a high pressure rating. This modification of the existing valve can provide space to implant a secondary valve apparatus within at least a portion of the existing valve, and maintain a relatively large effective orifice area (EOA).

In some embodiments, to facilitate this expansion or modification of the existing valve, elements in the valve frame of the existing valve can be configured to allow for radial deformation. Material selection and/or strut design can be engineered to accomplish the expansion. For example, in some embodiments, the previously or first implanted valve can be formed at least partially with a plastically deformable material, such as, for example, stainless steel or cobalt chromium. In some embodiments, all or a portion of the valve frame can be formed at least in part with a material that is not deformable, such as Nitinol, but include designed in breakaway regions to allow the valve to be modified. The breakaway regions can be formed, for example, with a material such as stainless steel or cobalt chromium. Similarly, a breakaway region can be of reduced dimension, creating a thin, frangible location which fractures and thus allows for frame expansion. In some embodiments, having a valve frame formed with a non-deformable material, the valve could include a locking mechanism to lock the valve into the deformed shape upon expansion. In some embodiments, it may be desired to have hinged frame elements to facilitate expansion or locking. In some cases, only a 10% diameter increase may be needed to provide the space needed to implant the secondary valve. In some cases, expansion up to 150% may be needed in the case of a valve with an inner frame with a very small diameter.

In some embodiments, a delivery system to deliver and implant a secondary prosthetic valve can include a balloon catheter to expand or modify an existing valve that can include a single balloon and single guidewire lumen that is offset from a centerline of the catheter. In some embodiments, a delivery system includes a balloon catheter that, to expand or modify an existing valve, includes multiple balloons and multiple guidewire lumens that are offset from a centerline of the catheter. The offset balloon(s) can prevent interaction with the ventricular portion (e.g., Nitinol tethers (described below), braided tether, etc.) of the existing valve during placement of the secondary valve inside the existing valve.

In some embodiments, a valve cup is provided that can be affixed on the atrial side of the existing implanted valve. Various different attachment methods can be used, such as, for example, barbs, hooks, or anchors. The valve cup can be delivered transseptally to avoid interference with the ventricular structure of the existing valve. The valve cup can create a duplicate valve within the existing prosthetic valve and maintain maximum EOA. In some cases, where the previously implanted valve has become stenotic, the valve can be expanded with a balloon catheter as mentioned above.

As described herein, in some embodiments, a prosthetic heart valve can include an outer frame and an inner frame coupled to the outer frame. The inner frame can include Nitinol tethers that are part of the ventricular portion of the inner frame, and a ventricular anchoring tether that can be coupled to a tether coupling portion disposed at a proximal end portion of the prosthetic heart valve. The anchoring tether can be used to secure the prosthetic heart valve within a desired position within the heart. The prosthetic heart valve can be formed with, for example, a shape-memory material and the anchoring tether can be, for example, formed with a braided filament.

In some embodiments described herein, where an implanted prosthetic valve includes a Nitinol tether portion of the valve and the valve becomes worn, deployment of a new prosthetic valve within the implanted valve can be more difficult. For such implanted prosthetic valves, delivery devices and methods are described herein to facilitate the deployment of a bioprosthetic valve to be implanted within the worn prosthetic valve. Such delivery devices and methods include transseptal delivery of the replacement valve and minimal interaction with the ventricular aspects (e.g., Nitinol tether portion) of the previously implanted bioprosthetic valve.

In some embodiments, the secondary valve apparatus can include a combination of radial force and clips that interact with the existing implanted valve to lock the secondary valve apparatus into position and prevent embolization from the existing valve. In some embodiments, the clips can have controlled actuation that allows for positioning of the secondary valve apparatus and clips multiple times to achieve an optimal positioning. In some embodiments, the secondary valve apparatus is secured to the existing valve with clips positioned on an atrium portion of the existing valve. In some embodiments, the secondary valve apparatus is secured to the existing valve with clips positioned on a ventricular portion of the existing valve.

In some embodiments, a secondary valve apparatus can be deployed within an existing surgical or transcatheter delivered prosthetic heart valve (e.g., mitral, tricuspid), other prosthetic heart apparatuses, such as, for example, an annuloplasty ring, a calcified annulus of a native heart valve, and/or to replace a percutaneous annuloplasty or other valve replacement/repair treatment, where the leaflets or repair have failed or the existing valve has become unstable.

In some embodiments, a secondary valve apparatus described herein can be deployed within at least a portion of an existing implanted prosthetic valve, and be anchored to a wall of the heart with a tether. For example, if an existing valve is secured to the heart not using an anchoring tether, the secondary tether can be delivered apically, deployed through a ventricular end portion of the existing valve, and anchored to a ventricular wall of the heart. The anchor of the secondary valve can secure a position of the unstable failed existing valve, anchor the secondary valve, and provide support to the left/right ventricle.

As background, a prosthetic heart valve can be delivered to a heart of a patient using a variety of different delivery approaches for delivering a prosthetic heart valve (e.g., prosthetic mitral valve). For example, the prosthetic heart valves described herein can be delivered using a transfemoral delivery approach as described in International Patent Application No. PCT/US15/14572 ("the '572 PCT Application") and International Patent Application No. PCT/US2016/012305 ("the '305 PCT Application"), the disclosures of which are hereby incorporated by reference herein, or via a transatrial approach or a transjugular approach such as described in U.S. Patent Application Pub. No. 2017/0079790 ("the '290 publication"), the disclosure of which is hereby incorporated by reference herein. The prosthetic valves described herein can also be delivered apically if desired.

In one example, where the prosthetic heart valve is a prosthetic mitral valve, the valve is placed within a lumen of a delivery sheath in a collapsed configuration. A distal end portion of a delivery sheath can be disposed within the left atrium of the heart, and the prosthetic valve can be moved out of the lumen of the delivery sheath and allowed to move to a biased expanded configuration. The prosthetic mitral valve can then be positioned within a mitral annulus of the heart.

Figure 2:
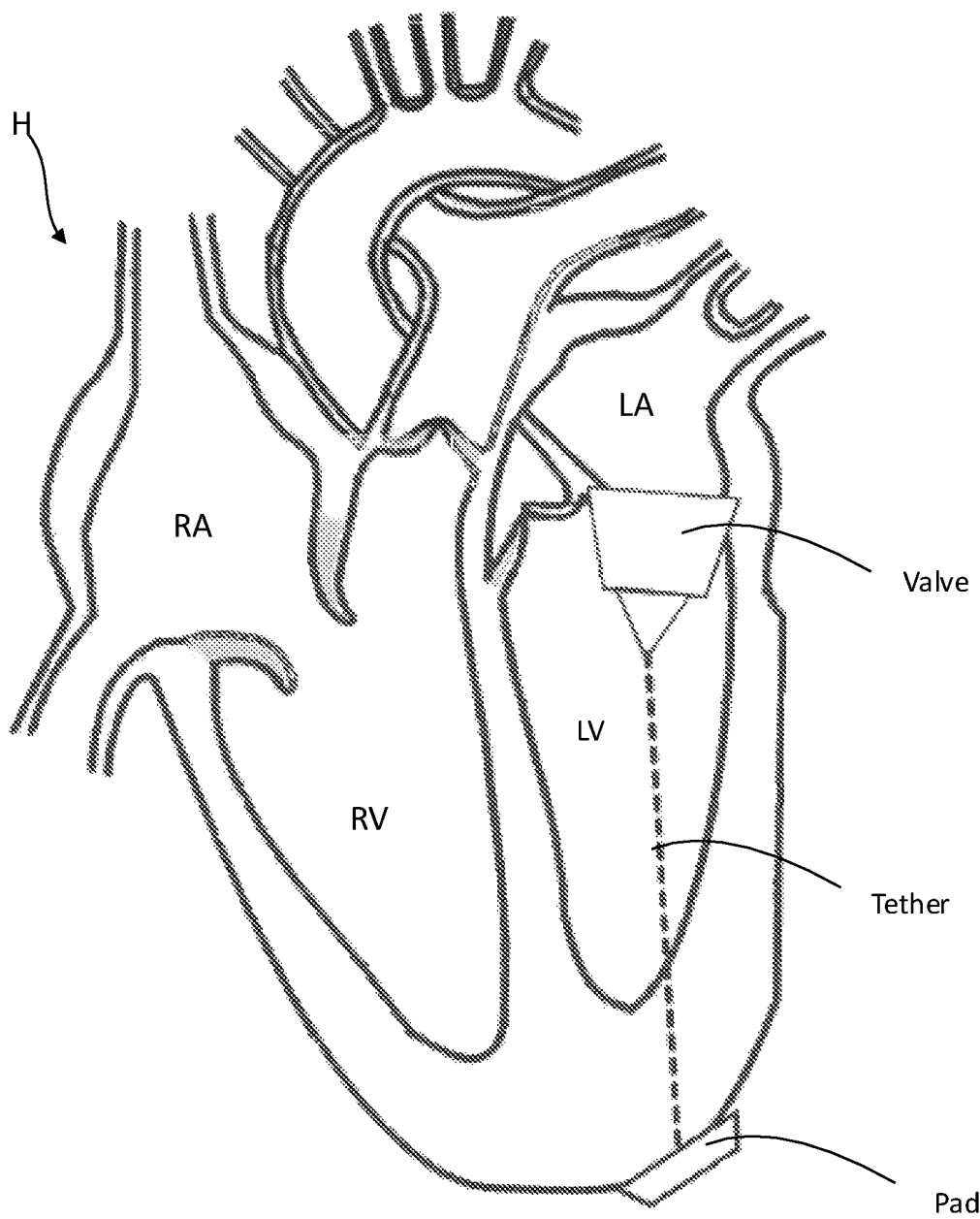
FIG. 2 is a schematic illustration of the prosthetic heart valve of FIG. 1 shown disposed within a heart.

FIG. 1 is a schematic illustration of an example prosthetic heart valve 100, within which a secondary valve apparatus can be deployed, or to which a secondary valve apparatus can be attached, if the prosthetic heart valve becomes worn and/or unstable as described above. FIG. 2 is a schematic illustration of an example prosthetic mitral valve deployed within a heart and anchored to a wall of the heart H with an epicardial pad via an anchoring tether. The prosthetic heart valve 100 (also referred to herein as "prosthetic valve" or "valve") can be, for example, a prosthetic mitral valve. The valve 100 can be delivered and deployed within an atrium of a heart using a variety of different delivery approaches including, for example, a transfemoral delivery approach, as described in the '572 PCT application and the '305 PCT application, or a transatrial approach or transjugular approach, as described in the '290 publication.

The valve 100 can include an outer frame assembly having an outer frame 120 and an inner valve assembly having an inner frame 150. Each of the outer frame 120 and the inner frame 150 can be formed as a tubular structure as described in more detail below with reference to FIGS. 3-14.

The outer frame 120 and the inner frame 150 can be coupled together at multiple coupling joints (not shown) disposed about a perimeter of the inner frame 150 and a perimeter of the outer frame 120. The valve 100 can also include other features, such as those described with respect to FIGS. 3-14 below. For illustration purposes, only the inner frame 150 and the outer frame 120 are discussed with respect to FIG. 1. The various characteristics and features of valve 100 described with respect to FIG. 1 can apply to any of the prosthetic valves described here.

The outer frame 120 is configured to have a biased expanded or undeformed shape and can be manipulated and/or deformed (e.g., compressed or constrained) and, when released, return to its original (expanded or undeformed) shape. For example, the outer frame can be formed of materials, such as metals or plastics, which have shape memory properties. With regards to metals, nickel titanium alloys such as nitinol have been found to be especially useful since they can be processed to be austenitic, martensitic or super elastic. Other shape memory alloys, such as Cu—Zn—Al—Ni alloys, and Cu—Al—Ni alloys, may also be used. The inner frame can be formed from a laser-cut tube of nitinol. The inner frame 150 can also have a biased expanded or undeformed shape and can be manipulated and/or deformed (e.g., compressed and/or constrained) and, when released, return to its original (expanded or undeformed) shape. Further details regarding the inner frame and the outer frame are described below with respect to valve 200 and FIGS. 3-14.

As shown in more detail with respect to inner frame 250 (see, e.g., FIGS. 6-8), the inner frame 150 can be formed from a laser-cut tube of nitinol. Inner frame 150 can be divided into four portions, corresponding to functionally different portions of the inner frame 150 in final form: atrial portion 147, body portion 142, strut portion 143, and tether clamp or connecting portion 144. In the schematic illustration of FIG. 1, the atrial and body portions (147 and 142) are within the outer frame 120, indicated by the dashed lines. The valve 100 also includes leaflets 170 disposed within a portion of the inner frame 150 (shown in dashed lines). The leaflets 170 can be formed and configured the same as or similar to the leaflets 270 described below with respect to FIGS. 3-14.

Figure 6:
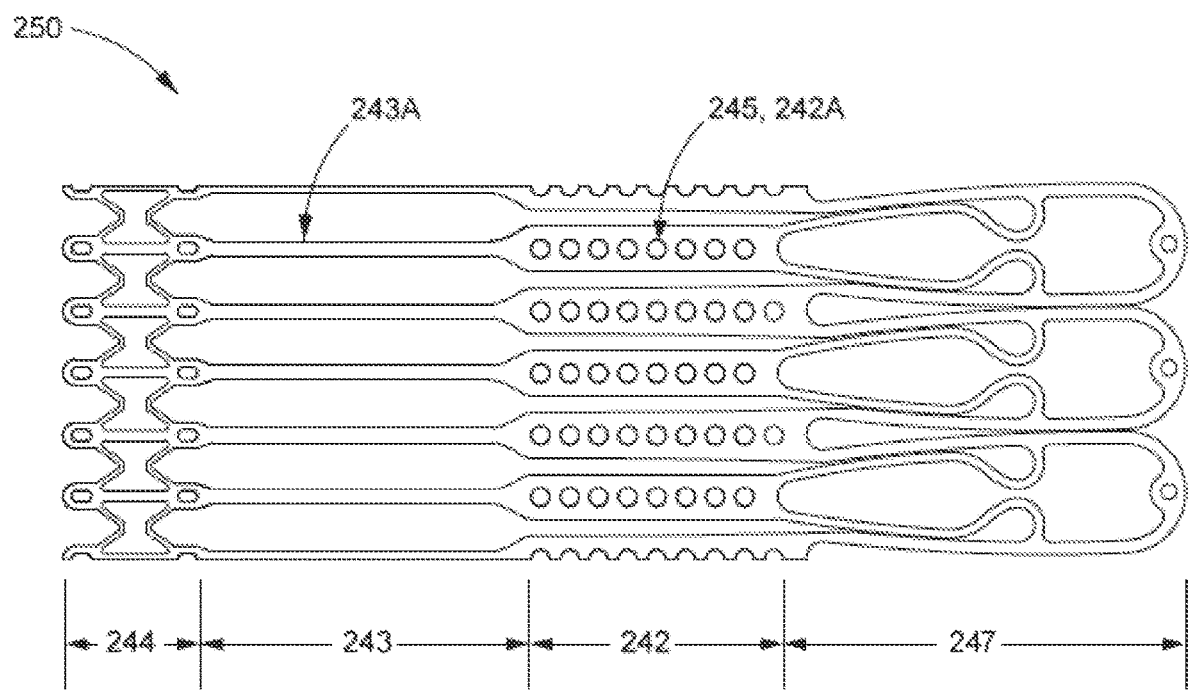
FIG. 6 is an opened and flattened view of the inner frame of the prosthetic heart valve of FIG. 3-5, in an unexpanded configuration.

The strut portion 143 of the inner frame 150 can include a suitable number of individual struts which connect the body portion 142 to the tether connecting portion 144. For example, FIG. 6 shows an inner frame 250 of an embodiment similar to inner frame 150 of FIG. 1. The inner frame 150 can be formed the same or similar way and include the same or similar portions and/or functions as inner frame 250 shown in FIG. 6.

The strut portion 143 of inner frame 150 can include struts (not shown in FIGS. 1, 2A and 2B) (see, e.g., struts 243a in FIG. 6) that connect the body portion 142 with the tether connecting portion 144. In some embodiments, the tether connecting portion 144 can include longitudinal extensions of the struts of the strut portion 143 that can be connected circumferentially by pairs of opposed, slightly V-shaped connecting members (or "micro-Vs") (see, e.g., inner frame 250 in FIG. 6). For example, in some embodiments, the strut portion 143 can include six struts that extend to form six struts of the tether connecting portion 144, with each of the six struts of the tether connecting portion 144 connected circumferentially by micro-Vs.

The tether connecting portion or the coupling portion 144 (also referred to as first end portion of inner frame 150) can be configured to be radially collapsible by application of a compressive force as described in more detail below with reference to valve 200 and inner frame 250. Thus, tether connecting portion 144 can be configured to compressively clamp or grip one end of a tether 136 (e.g. braided filament line), either connecting directly onto the tether 136 or onto an intermediate structure, such as a polymer or metal piece that is in turn firmly fixed to the tether 136. The tether connecting portion 144 can also include openings (not shown in FIG. 1) through which sutures or wires can be inserted to fasten around the collapsed struts and around the end of the tether 136 to couple the tether 136 to the tether connecting portion 144. The tether 136 may be secured to an epicardial pad 139, which in turn may be fixed to an outer surface of the heart.

Figure 3:
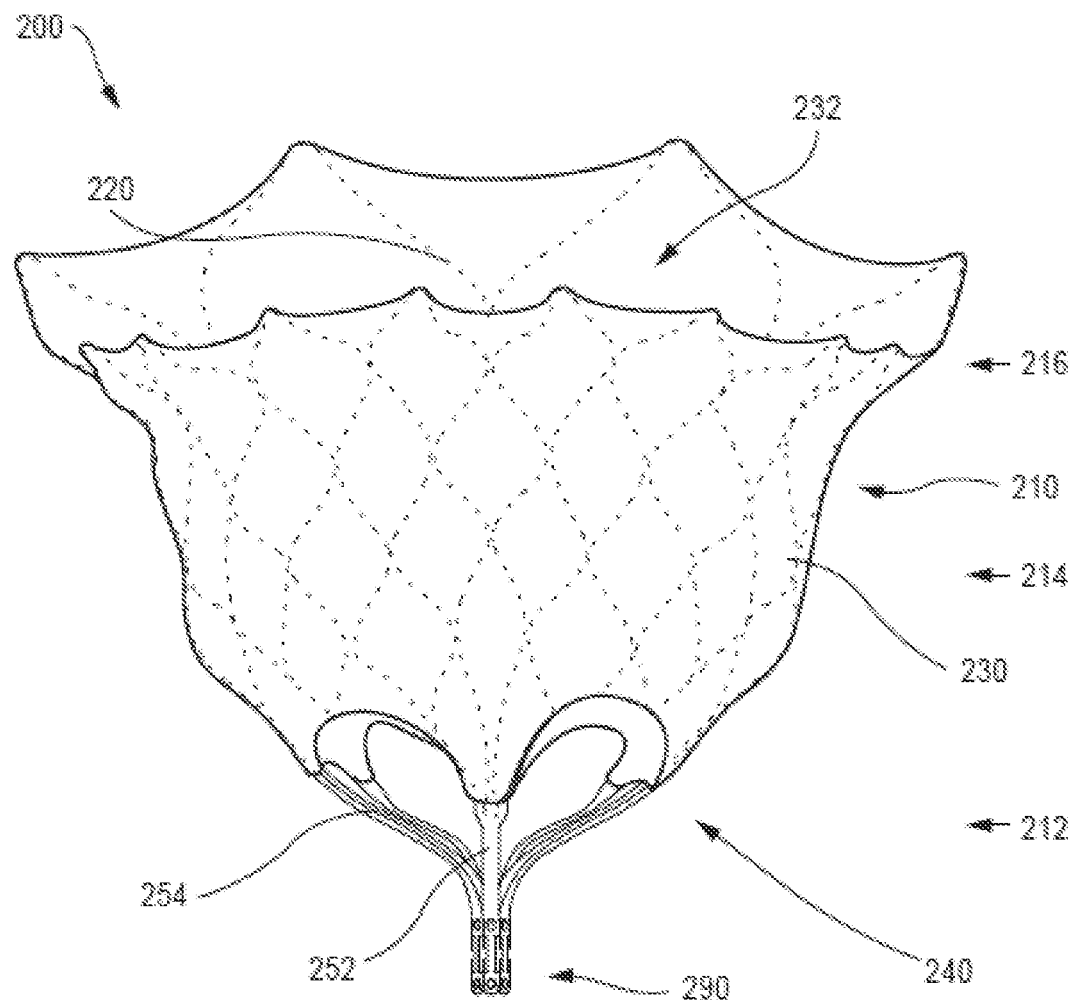
FIGS. 3-5 are front, bottom, and top views of a prosthetic heart valve according to an embodiment.
Figure 4:
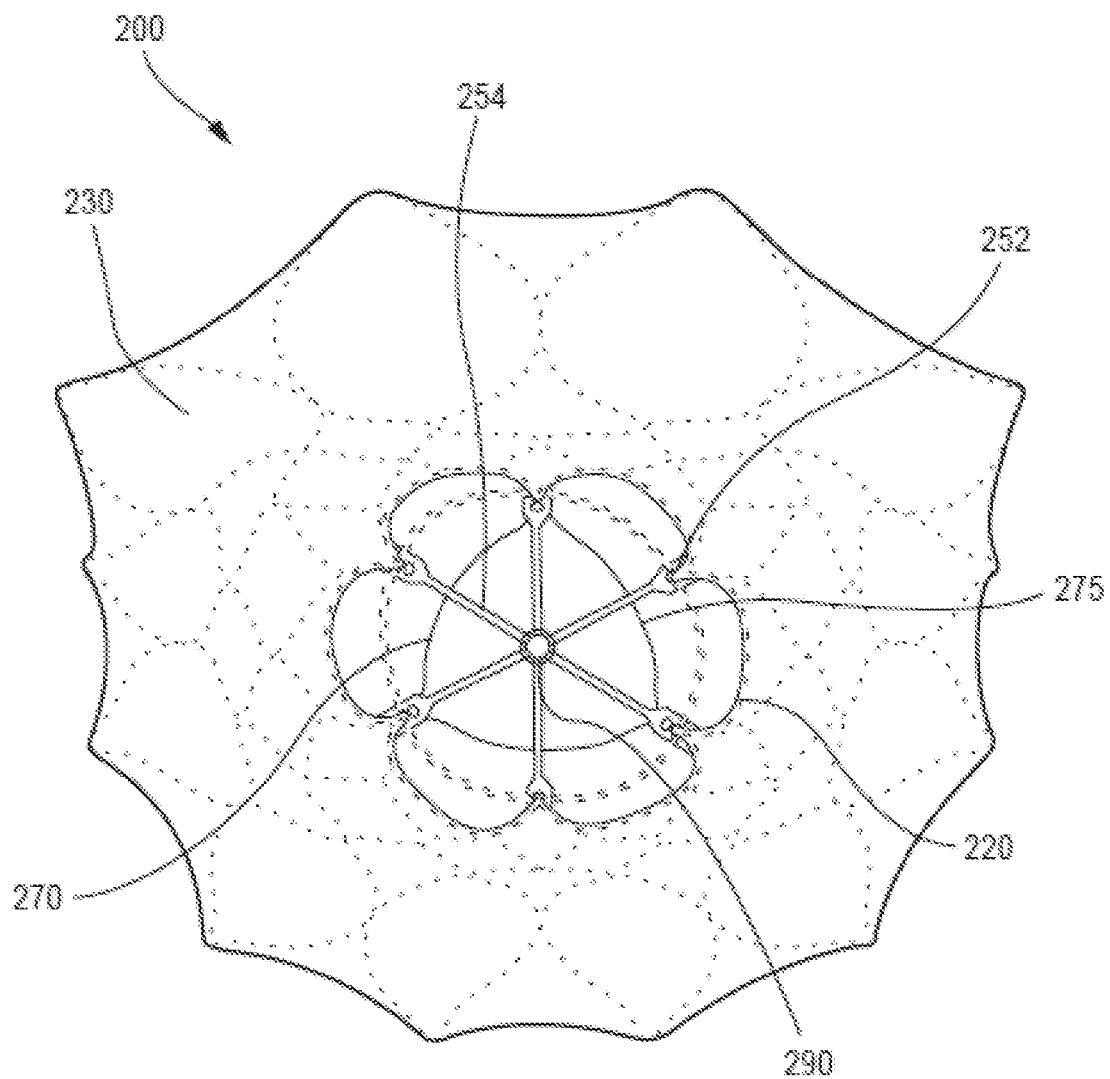
Figure 5:
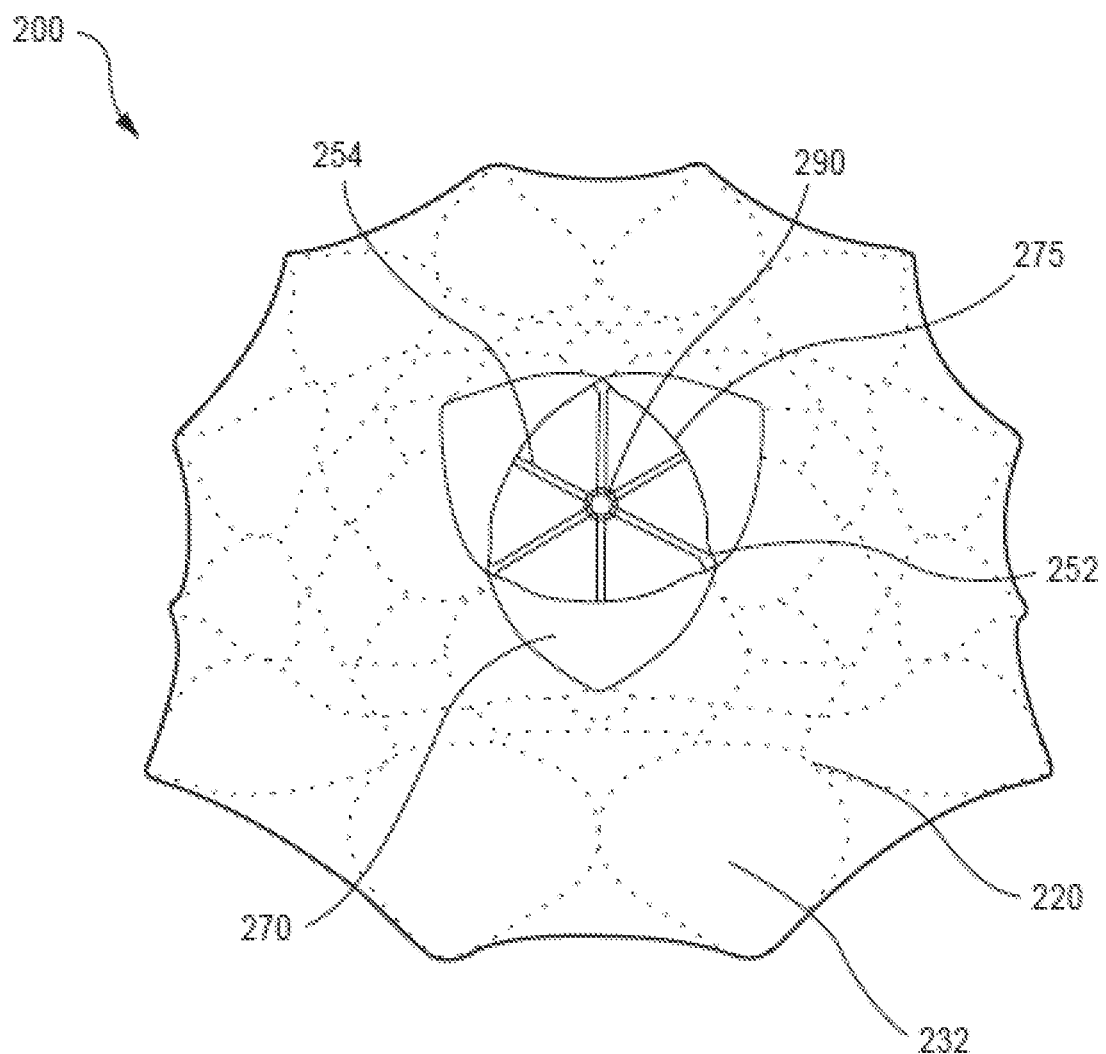

FIGS. 3-14 illustrate another embodiment of a prosthetic heart valve in which a secondary valve apparatus can be deployed or to which a secondary valve apparatus may be attached. FIGS. 3-5 are front, bottom, and top views, respectively, of a prosthetic heart valve 200 according to an embodiment. The prosthetic heart valve 200 can be delivered and deployed within a left atrium of a heart using a variety of different delivery approaches including, for example, a transfemoral delivery approach or a transatrial delivery approach. Prosthetic heart valve 200 (also referred to herein as "valve" or "prosthetic valve") is designed to replace a damaged or diseased native heart valve such as a mitral valve. Valve 200 includes an outer frame assembly 210 and an inner valve assembly 240 coupled to the outer frame assembly 210.

As shown, outer frame assembly 210 includes an outer frame 220, covered on all or a portion of its outer face with an outer covering 230, and covered on all or a portion of its inner face by an inner covering 232. Outer frame 220 can provide several functions for prosthetic heart valve 200, including serving as the primary structure, as an anchoring mechanism and/or an attachment point for a separate anchoring mechanism to anchor the valve to the native heart valve apparatus, a support to carry inner valve assembly 240, and/or a seal to inhibit paravalvular leakage between prosthetic heart valve 200 and the native heart valve apparatus.

Outer frame 220 has a biased expanded configuration and can be manipulated and/or deformed (e.g., compressed and/or constrained) and, when released, return to its original unconstrained shape. To achieve this, outer frame 220 can be formed of materials, such as metals or plastics that have shape memory properties. With regards to metals, nitinol has been found to be especially useful since it can be processed to be austenitic, martensitic or super elastic. Other shape memory alloys, such as Cu—Zn—Al—Ni alloys, and Cu—Al—Ni alloys, may also be used.

As best shown in FIG. 3, outer frame assembly 210 has an upper end (e.g., at the atrium portion 216), a lower end (e.g., at the ventricle portion 212), and a medial portion (e.g., at the annulus portion 214) therebetween. The upper end or atrium portion 216 (also referred to as "outer free end portion") defines an open end portion of the outer frame assembly 210. The medial or annulus portion 214 of the outer frame assembly 210 has a perimeter that is configured (e.g., sized, shaped) to fit into an annulus of a native atrioventricular valve. The upper end of the outer frame assembly 210 has a perimeter that is larger than the perimeter of the medial portion. In some embodiments, the perimeter of the upper end of the outer frame assembly 210 has a perimeter that is substantially larger than the perimeter of the medial portion. As shown best in FIG. 5, the upper end and the medial portion of the outer frame assembly 210 has a D-shaped cross-section. In this manner, the outer frame assembly 210 promotes a suitable fit into the annulus of the native atrioventricular valve.

Inner valve assembly 240 includes an inner frame 250, an outer covering (not shown), and leaflets 270. As shown, the inner valve assembly 240 includes an upper portion having a periphery formed with multiple arches. The inner frame 250 includes six axial posts or frame members that support the outer covering of the inner valve assembly and leaflets 270. Leaflets 270 are attached along three of the posts, shown as commissure posts 252 (best illustrated in FIG. 4), and the outer covering of the inner valve assembly 240 is attached to the other three posts, 254 (best illustrated in FIG. 4), and optionally to commissure posts 252. Each of the outer covering of the inner valve assembly 240 and leaflets 270 are formed of approximately rectangular sheets of material, which are joined together at their upper, or atrium end. The lower, ventricle end of the outer covering may be joined to inner covering 232 of outer frame assembly 210, and the lower, ventricle end of leaflets 270 may form free edges 275, though coupled to the lower ends of commissure posts 252.

Although inner valve assembly 240 is shown as having three leaflets, in other embodiments, an inner valve assembly can include any suitable number of leaflets. The leaflets 270 are movable between an open configuration and a closed configuration in which the leaflets 270 coapt, or meet in a sealing abutment.

Outer covering 230 of the outer frame assembly 210 and inner covering 232 of outer frame assembly 210, outer covering of the inner valve assembly 240 and leaflets 270 of the inner valve assembly 240 may be formed of any suitable material, or combination of materials, such as those discussed above. In this embodiment, the inner covering 232 of the outer frame assembly 210, the outer covering of the inner valve assembly 240, and the leaflets 270 of the inner valve assembly 240 are formed, at least in part, of porcine pericardium. Moreover, in this embodiment, the outer covering 230 of the outer frame assembly 210 is formed, at least in part, of polyester.

Figure 7:
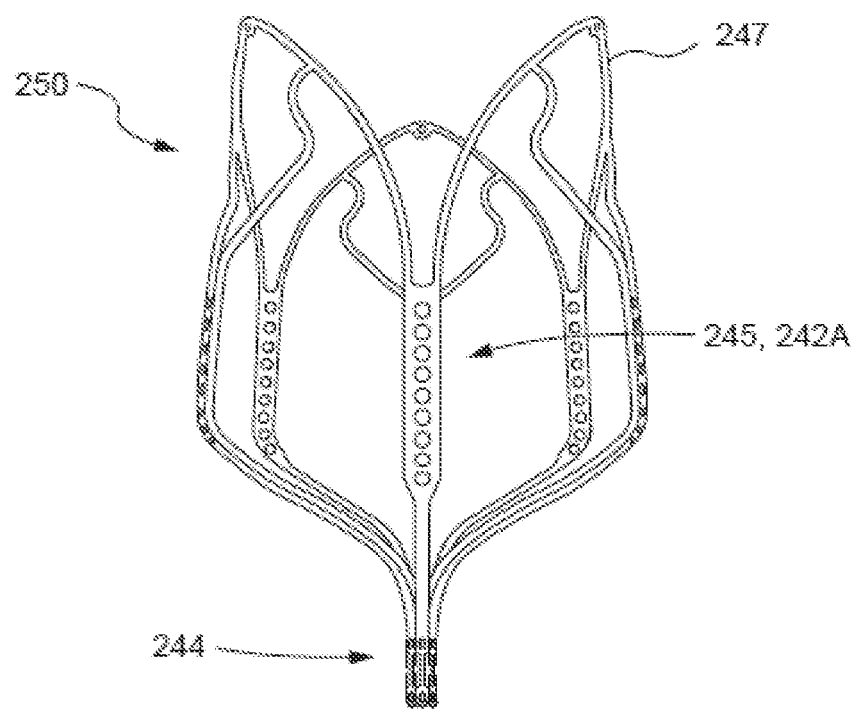
FIGS. 7 and 8 are side and bottom views, respectively, of the inner frame of FIG. 6 in an expanded configuration.
Figure 8:
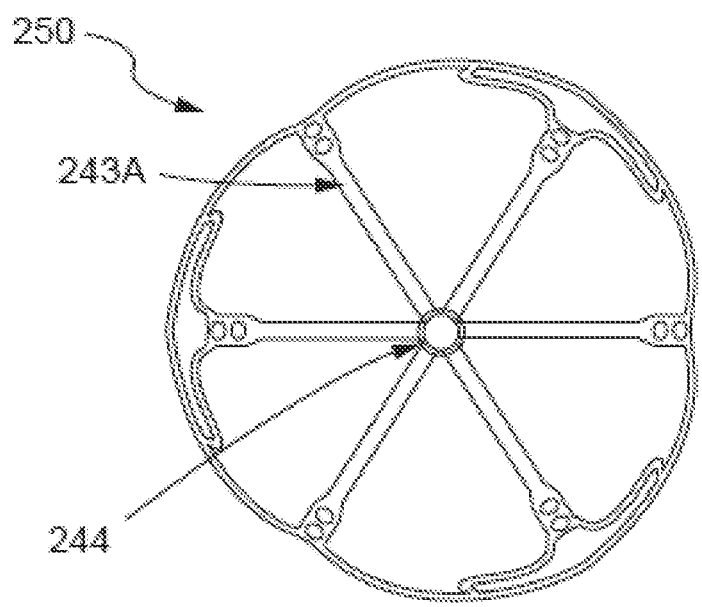

Inner frame 250 is shown in more detail in FIGS. 6-8. Specifically, FIGS. 6-8 show inner frame 250 in an undeformed, initial state (FIG. 6), a side view of the inner frame 250 in an expanded configuration (FIG. 7), and a bottom view of the inner frame 250 in the expanded configuration (FIG. 8), respectively, according to an embodiment.

In this embodiment, inner frame 250 is formed from a laser-cut tube of nitinol. Inner frame 250 is illustrated in FIG. 6 in an undeformed, initial state, e.g. as laser-cut, but cut and unrolled into a flat sheet for ease of illustration. Inner frame 250 can be divided into four portions, corresponding to functionally different portions of the inner frame 250 in final form: atrial portion 247, body portion 242, strut portion 243, and tether clamp or connecting portion 244. Strut portion 243 includes six struts, such as strut 243A, which connect body portion 242 to tether connecting portion 244.

Tether connecting portion 244 (also referred to as first end portion of inner frame) includes longitudinal extensions of the struts, connected circumferentially by pairs of opposed, slightly V-shaped connecting members (or "micro-Vs"). Tether connecting portion 244 is configured to be radially collapsed by application of a compressive force, which causes the micro-Vs to become more deeply V-shaped, with the vertices moving closer together longitudinally and the open ends of the V shapes moving closer together circumferentially. Thus, tether connecting portion 244 can be configured to compressively clamp or grip one end of a tether, either connecting directly onto a tether line (e.g., braided filament line) or onto an intermediate structure, such as a polymer or metal piece that is in term firmly fixed to the tether line.

In contrast to tether connecting portion 244, atrial portion 247 (also referred to as "inner frame free end portion") and body portion 242 are configured to be expanded radially. Strut portion 243 forms a longitudinal connection and radial transition between the expanded body portion and the compressed tether connecting portion 244. Body portion 242 provides an inner frame coupling portion 245 that includes six longitudinal posts, such as post 242A. The inner frame coupling portion 245 can be used to attach leaflets 270 to inner frame 240, and/or can be used to attach inner assembly 240 to outer assembly 210, such as by connecting inner frame 250 to outer frame 220. In the illustrated embodiment, the posts include openings through which connecting members (such as suture filaments and/or wires) can be passed to couple the posts to other structures.

Inner frame 250 is shown in a fully deformed, e.g., the final, deployed configuration, in side view and bottom view in FIGS. 7 and 8, respectively.

Figure 9:
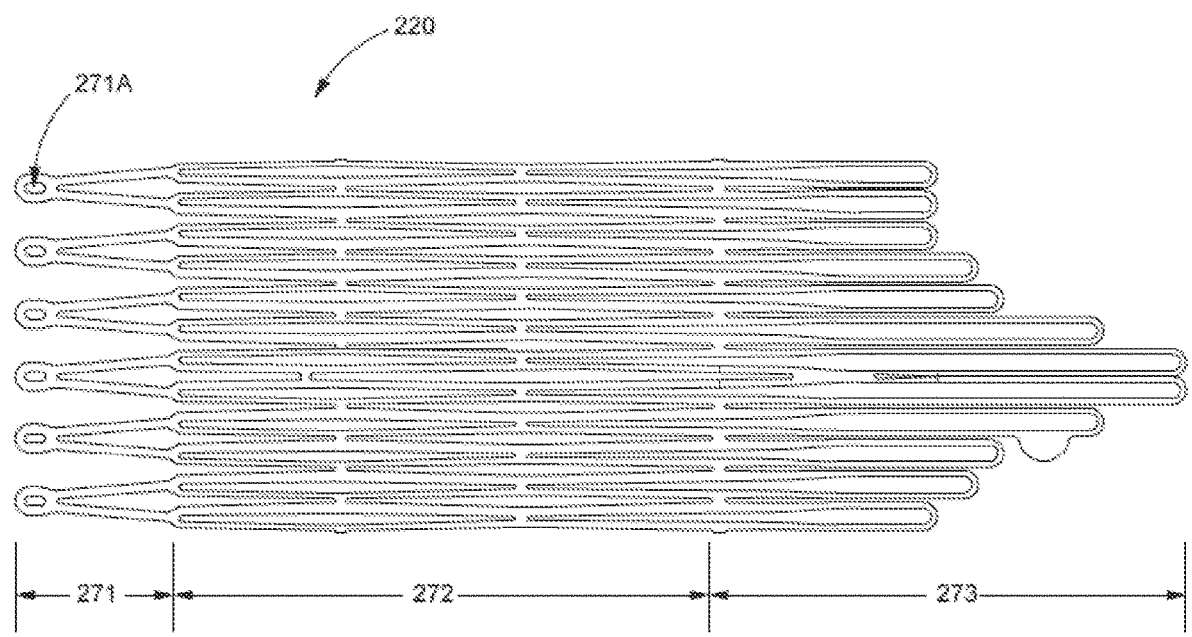
FIG. 9 is an opened and flattened view of the outer frame of the valve of FIGS. 3-5, in an unexpanded configuration.
Figure 10:
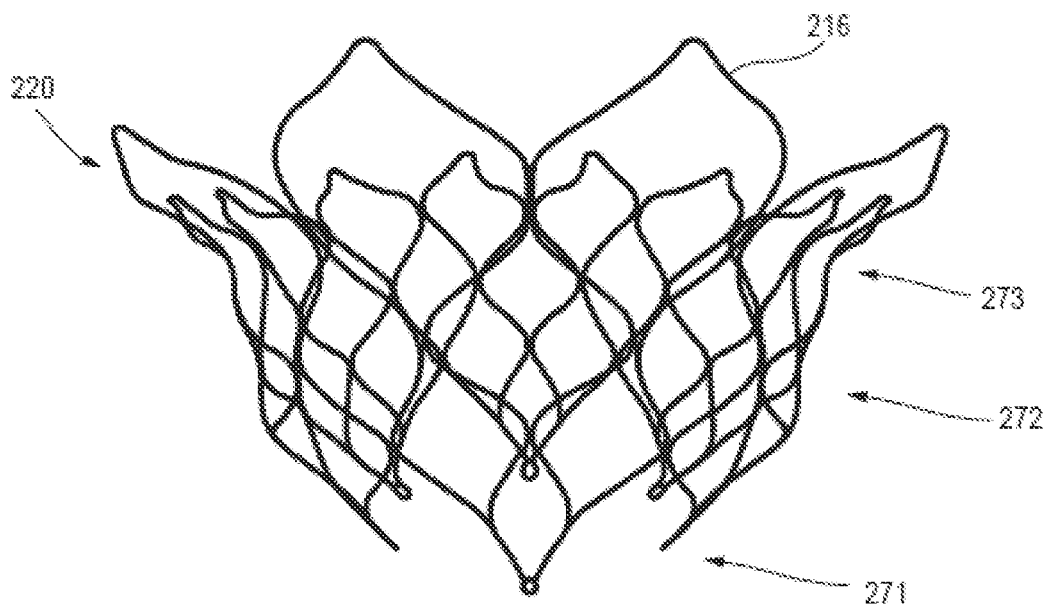
FIGS. 10 and 11 are side and top views, respectively, of the outer frame of FIG. 9 in an expanded configuration.
Figure 11:
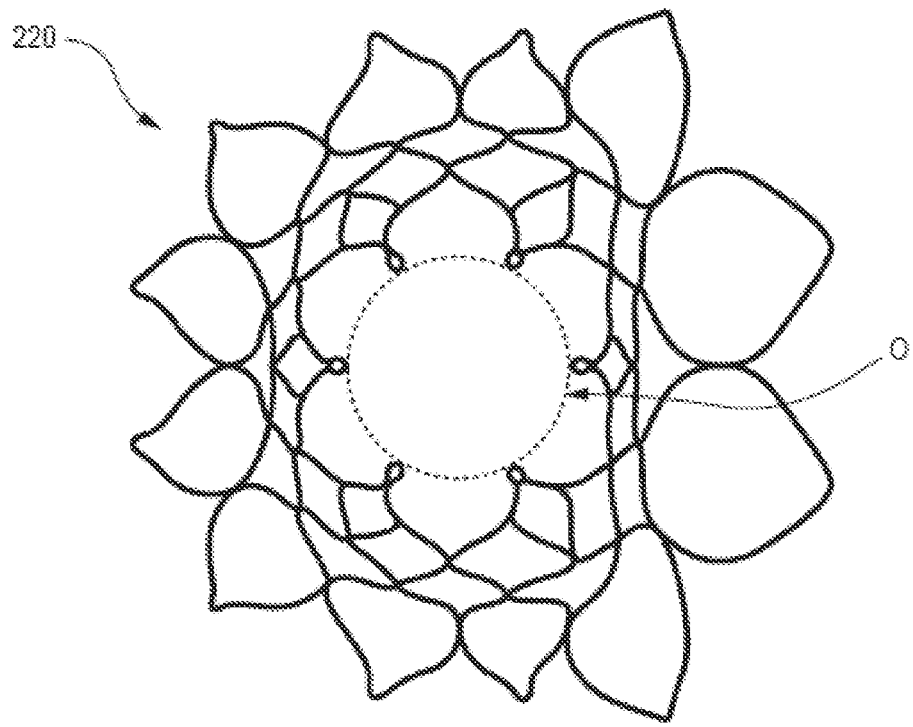

Outer frame 220 of valve 200 is shown in more detail in FIGS. 9-11. In this embodiment, outer frame 220 is also formed from a laser-cut tube of nitinol. Outer frame 220 is illustrated in FIG. 9 in an undeformed, initial state, e.g., as laser-cut, but cut and unrolled into a flat sheet for ease of illustration. Outer frame 220 can be divided into an outer frame coupling portion 271, a body portion 272, and a cuff portion 273 (which includes the atrium or free end portion 216), as shown in FIG. 9. Outer frame coupling portion 271 includes multiple openings or apertures, such as 271A, by which outer frame 220 can be coupled to inner frame 250, as discussed in more detail below.

Outer frame 220 is shown in a fully deformed, e.g., the final, deployed configuration, in side view and top view in FIGS. 10 and 11, respectively. As best seen in FIG. 11, the lower end of outer frame coupling portion 271 forms a roughly circular opening (identified by "O" in FIG. 11). The diameter of this opening preferably corresponds approximately to the diameter of body portion 242 of inner frame 250, to facilitate coupling of the two components of valve 200.

Figure 12:
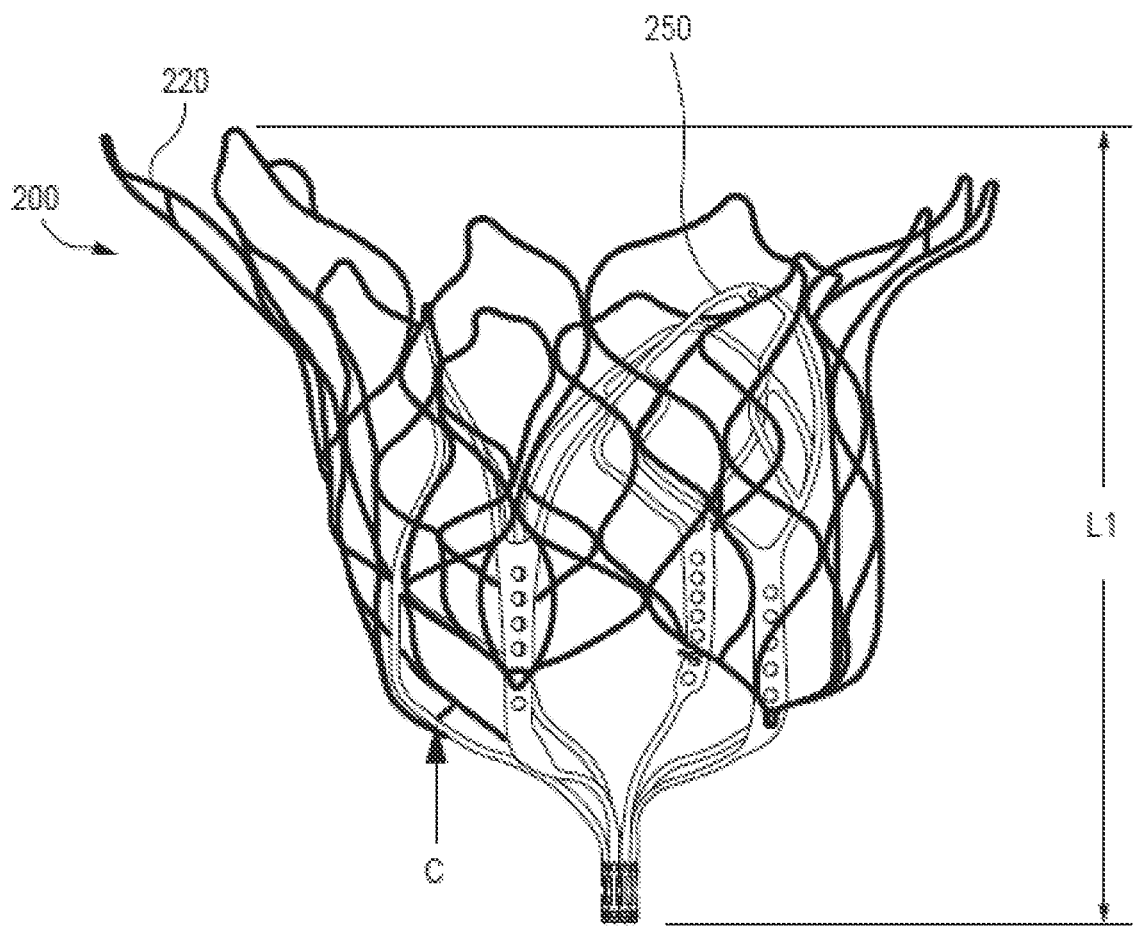
FIG. 12-14 are side, front, and top views of an assembly of the inner frame of FIGS. 6-8 and the outer frame of FIGS. 9-11.
Figure 13:
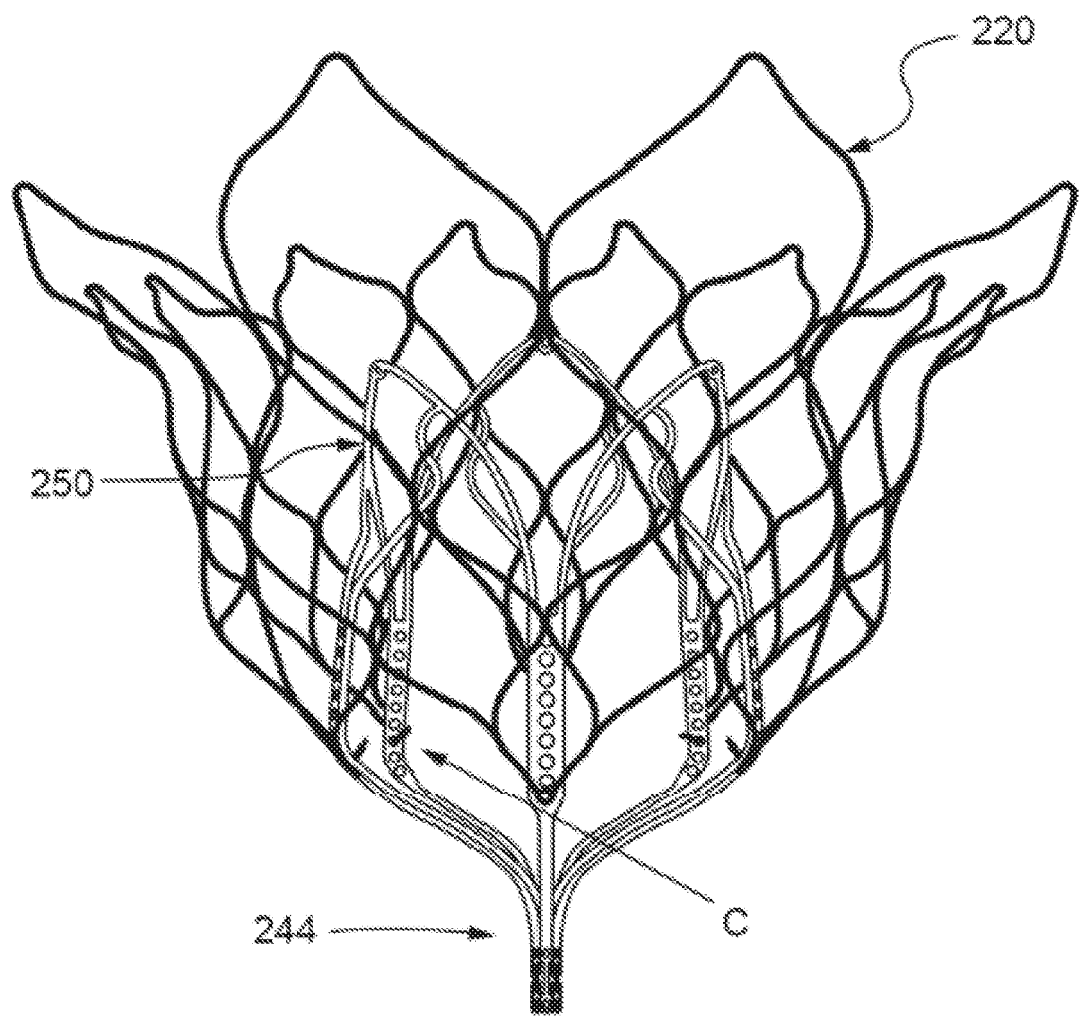
Figure 14:
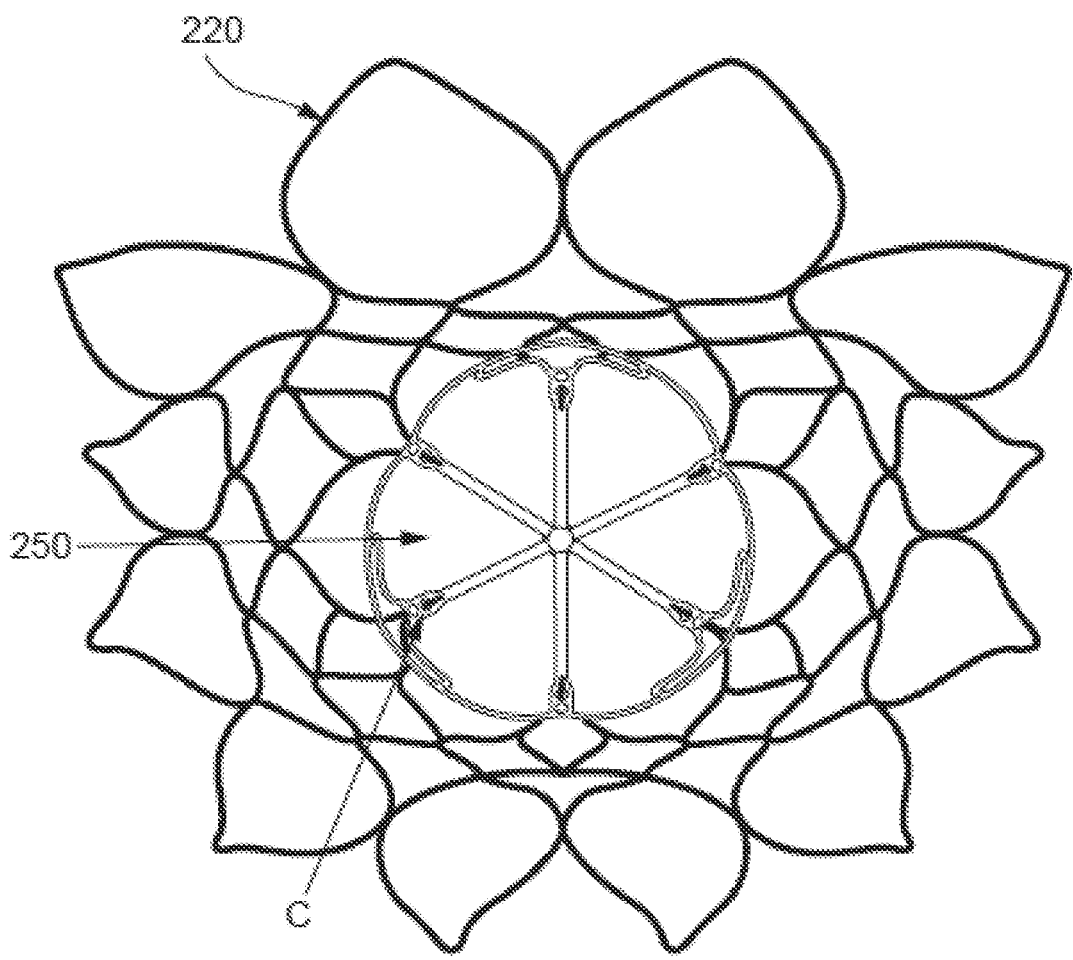

Outer frame 220 and inner frame 250 are shown coupled together in FIGS. 12-14, in front, side, and top views, respectively. The two frames collectively form a structural support for a prosthetic valve such as valve 200. The frames support the valve leaflet structure (e.g., leaflets 270) in the desired relationship to the native valve annulus, support the coverings (e.g., outer covering 230, inner covering 232, outer covering of inner valve assembly 240) for the two frames to provide a barrier to blood leakage between the atrium and ventricle, and couple to a tether (not shown in FIGS. 3-14) (e.g., tether 136 described above with respect to FIG. 1) to aid in holding the prosthetic valve 200 in place in the native valve annulus by the tether connection to the ventricle wall. The outer frame 220 and the inner frame 250 are connected at six coupling points (representative points are identified as "C" in FIGS. 12-14). In this embodiment, the coupling points are implemented with a mechanical fastener, such as a short length of wire, passed through an aperture (such as aperture 271A) in outer frame coupling portion 271 and corresponding openings in inner frame coupling portion 245 (e.g., longitudinal posts, such as post 242A) in body portion 242 of inner frame 250. Inner frame 250 is thus disposed within the outer frame 220 and securely coupled to it.

FIGS. 15-21 illustrate a method of reconfiguring a prosthetic heart valve 300 (e.g., prosthetic mitral valve) prior to inserting the prosthetic heart valve 300 into a delivery sheath 326 (see, e.g., FIGS. 17-21) for delivery into the atrium of the heart. The prosthetic heart valve 300 (also referred to herein as "valve") can be constructed the same as or similar to, and function the same as or similar to the valves 100 and 200 described above. Thus, some details regarding the valve 300 are not described below. It should be understood that for features and functions not specifically discussed, those features and functions can be the same as or similar to the valve 200.

Figure 15:
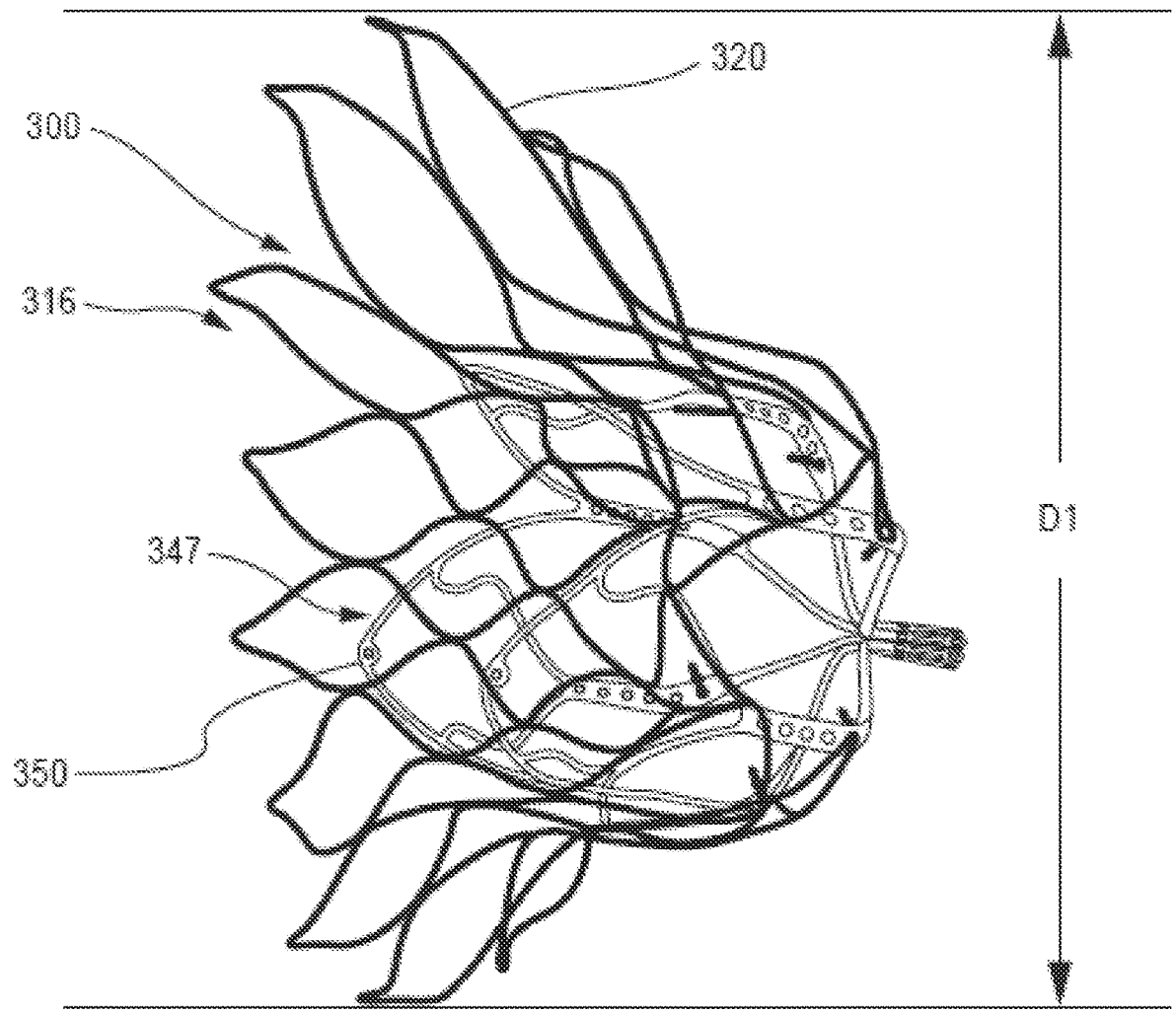
FIG. 15 is a side perspective view of an assembly of an inner frame and an outer frame shown in a biased expanded configuration, according to an embodiment.
Figure 16:
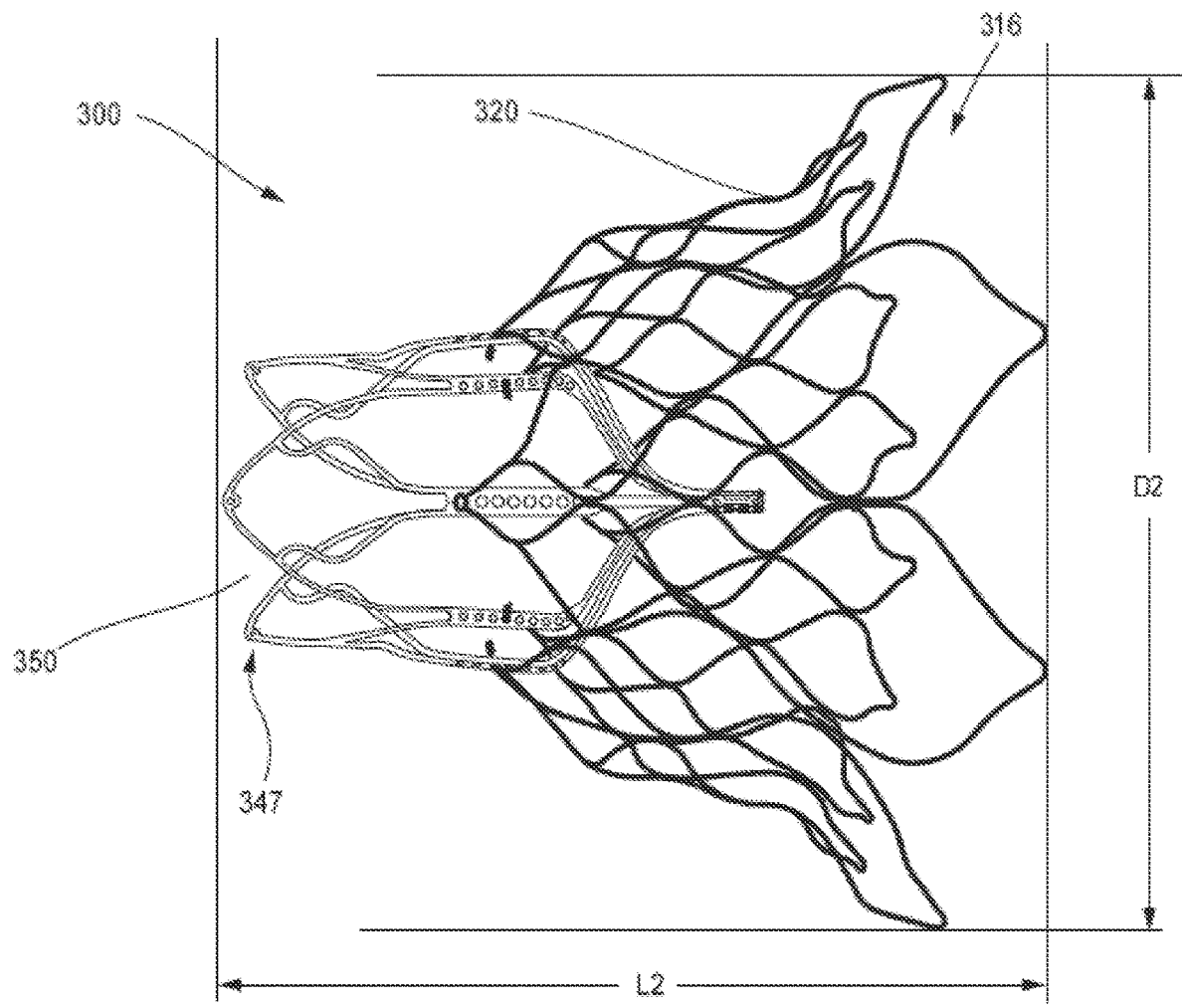
FIG. 16 is a side perspective view of the assembly of FIG. 15 with the outer frame shown inverted.
Figure 17:
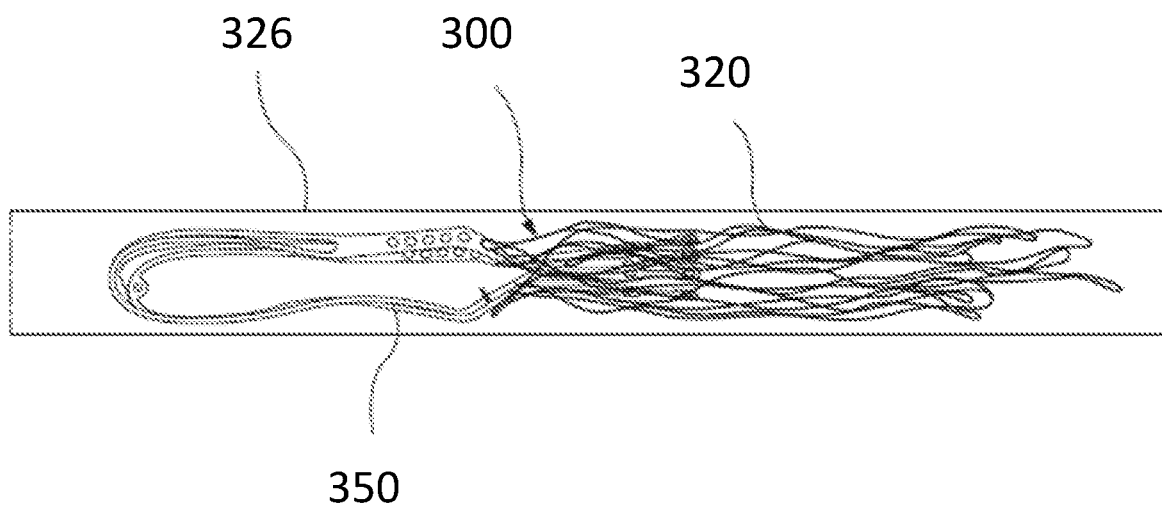
FIG. 17 is side view of the assembly of FIG. 16 shown in a collapsed configuration within a lumen of a delivery sheath.

As shown in FIG. 15, the valve 300 has an outer frame 320 and an inner frame 350. As discussed above for valves 100 and 200, the outer frame 320 and the inner frame 350 of valve 300 can each be formed with a shape-memory material and have a biased expanded configuration. The outer frame 320 and the inner frame 350 can be moved to a collapsed configuration for delivery of the valve 300 to the heart. In this example method of preparing the valve 300 for delivery to the heart, the outer frame 320 of the valve 300 is first disposed in a prolapsed or inverted configuration as shown in FIG. 16. Specifically, the elastic or superelastic structure of outer frame 320 of valve 300 allows the outer frame 320 to be disposed in the prolapsed or inverted configuration prior to the valve 300 being inserted into the lumen of the delivery sheath 326. As shown in FIG. 16, to dispose the outer frame 320 in the inverted configuration, the outer frame 320 is folded or inverted distally (to the right in FIG. 16) such that an open free end 316 of the outer frame 320 is pointed away from an open free end 347 of the inner frame 350. As described above for valve 100, in this inverted configuration, the overall outer perimeter or outer diameter of the valve 300 may be reduced or may be substantially the same, while the overall length is increased. For example, the diameter D1 shown in FIG. 15 is greater than the diameter D2 shown in FIG. 16, and the length L1 (shown in FIG. 12 for valve 200) is less than the length L2 shown in FIG. 16 for valve 300. With the outer frame 320 in the inverted configuration relative to the inner frame 350, the valve 300 can be placed within a lumen of a delivery sheath 326 as shown in FIG. 17 for delivery of the valve 300 to the left atrium of the heart. By disposing the outer frame 320 in the inverted configuration relative to the inner frame 350, the valve 300 can be collapsed into a smaller overall diameter, e.g. when placed in a smaller diameter delivery sheath, than would be possible if the valve 300 in the configuration shown in FIG. 15 were collapsed radially without being inverted. This is because in the configuration shown in FIG. 15, the two frames are concentric or nested, and thus the outer frame 320 must be collapsed around the inner frame 350, whereas in the configuration shown in FIG. 16, the two frames are substantially coaxial but not concentric or nested. Thus, in the configuration shown in FIG. 16 the outer frame 320 can be collapsed without the need to accommodate the inner frame 350 inside of it. In other words, with the inner frame 350 disposed mostly inside or nested within the outer frame 320, the layers or bulk of the frame structures cannot be compressed to as small a diameter. In addition, if the frames are nested, the structure is less flexible, and therefore, more force is needed to bend the valve, e.g. to pass through tortuous vasculature or to make a tight turn in the left atrium after passing through the atrial septum to be properly oriented for insertion into the mitral valve annulus.

Figure 22:
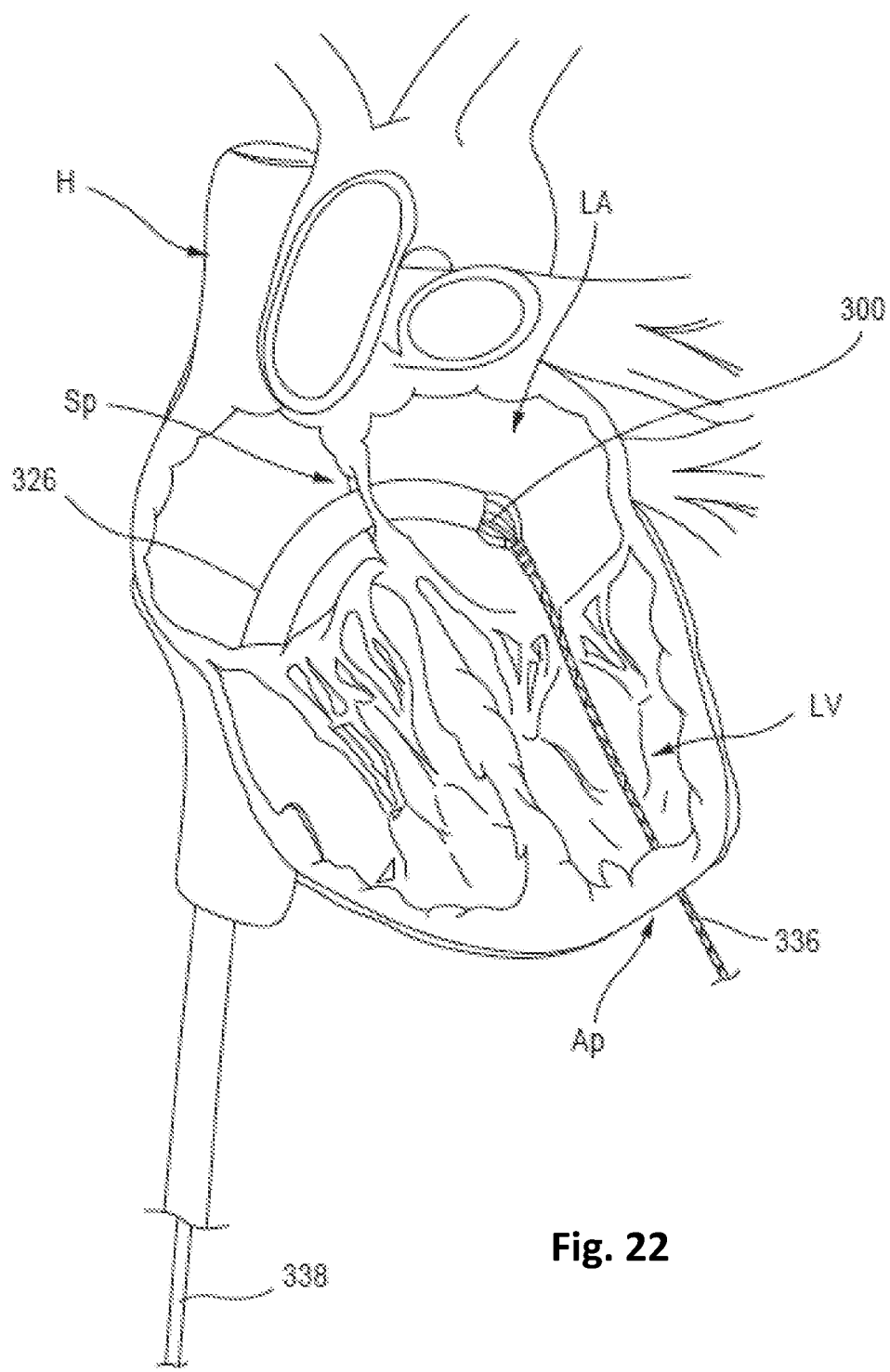
FIGS. 22-24 illustrate steps of a portion of a method to deliver the prosthetic valve of FIGS. 15-21 to an atrium of a heart and within the native mitral annulus.
Figure 23:
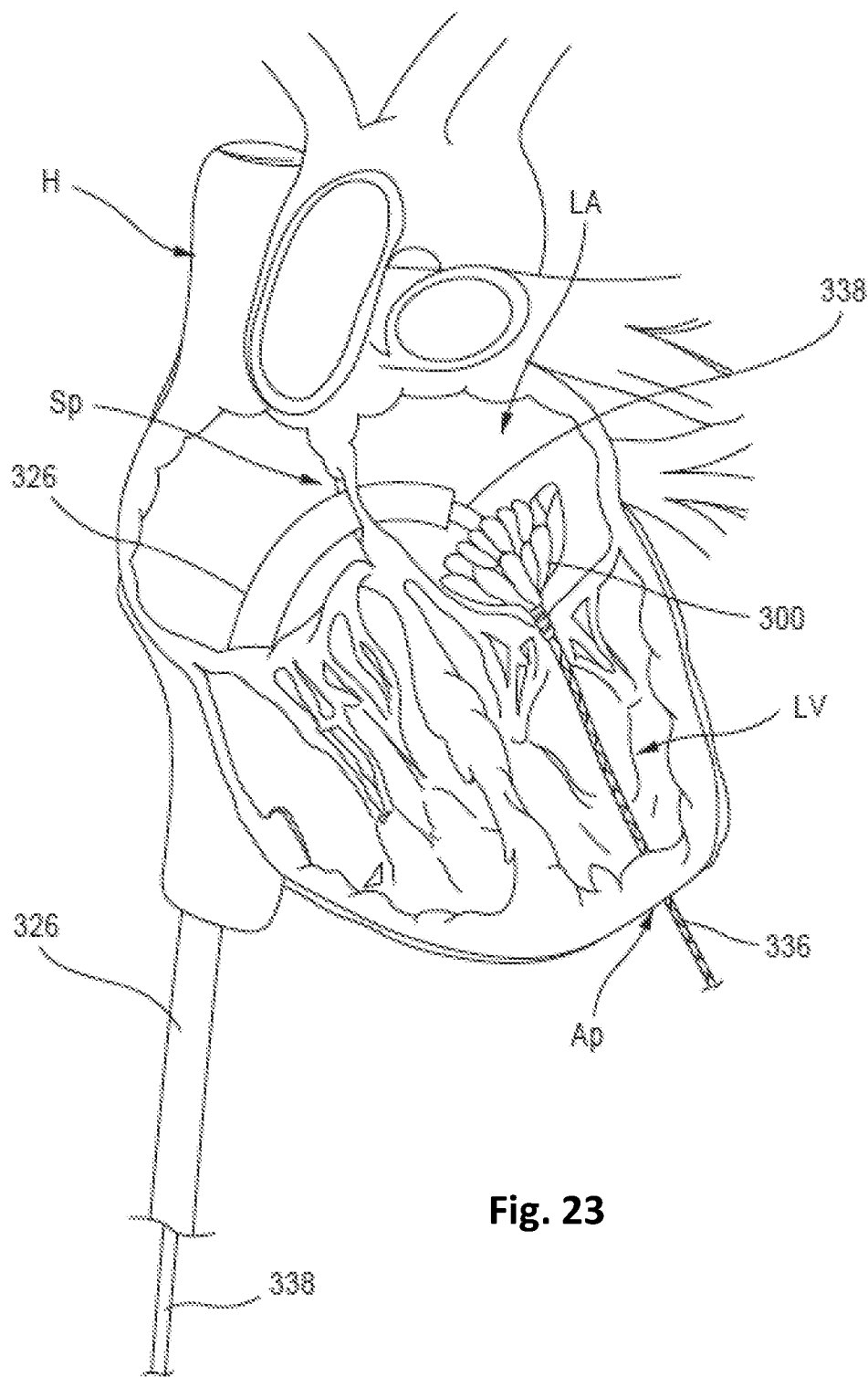
Figure 24:
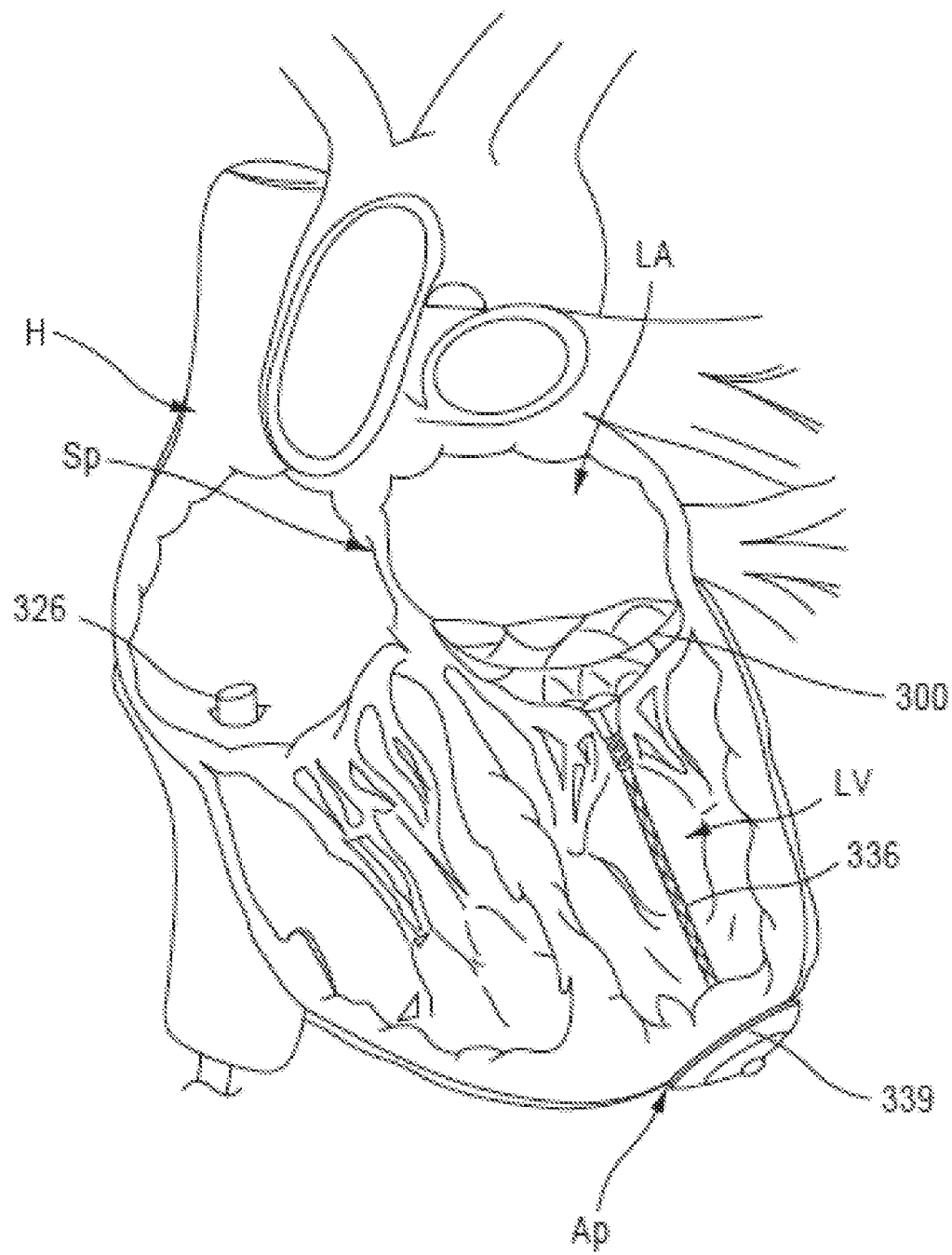

FIGS. 22-24 illustrate a portion of a procedure to deliver the valve 300 to the heart. In this embodiment, the valve 300 is shown being delivered via a transfemoral delivery approach as described, for example, in the '305 PCT application incorporated by reference above. The delivery sheath 326, with the valve 300 disposed within a lumen of the delivery sheath 326 and in an inverted configuration as shown in FIG. 17, can be inserted into a femoral puncture, through the femoral vein, through the inferior vena cava, into the right atrium, through the septum Sp and into the left atrium LA of the heart. With the distal end portion of the delivery sheath 326 disposed within the left atrium of the heart, the valve 300 can be deployed outside a distal end of the delivery sheath 326. For example, in some embodiments, a pusher device 338 can be used to move or push the valve 300 out the distal end of the delivery sheath 326. As shown in FIGS. 22-24, a tether 336 can be attached to the valve 300, and extend though the mitral annulus, through the left ventricle LV, and out a puncture site at the apex Ap. In some embodiments, the valve 300 can be moved out of the delivery sheath 326 by pulling proximally on the tether 336. In some embodiments, the valve 300 can be deployed by pushing with the pusher device and pulling with the tether.

Figure 18:
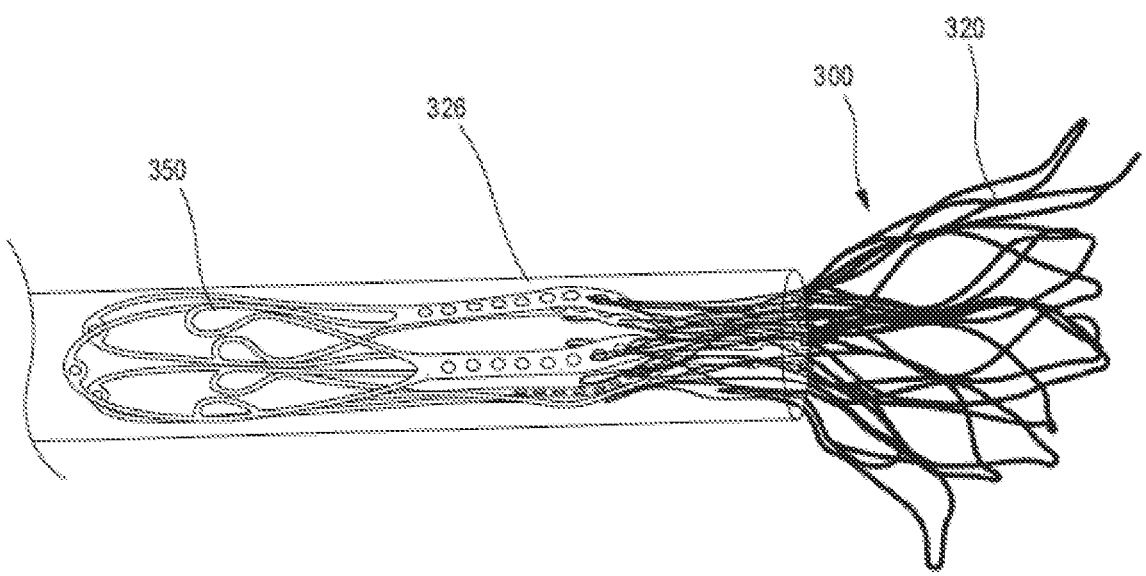
FIG. 18 is a side view of the assembly of FIG. 17 shown in a first partially deployed configuration.
Figure 19:
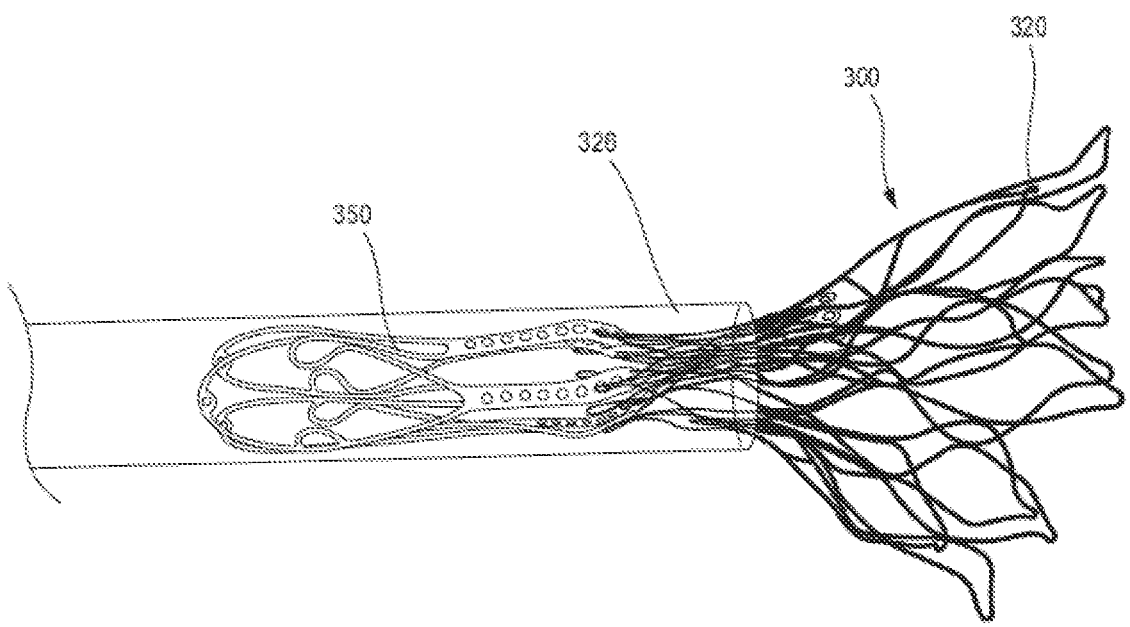
FIG. 19 is a side view of the assembly of FIG. 17 shown in a second partially deployed configuration.
Figure 20:
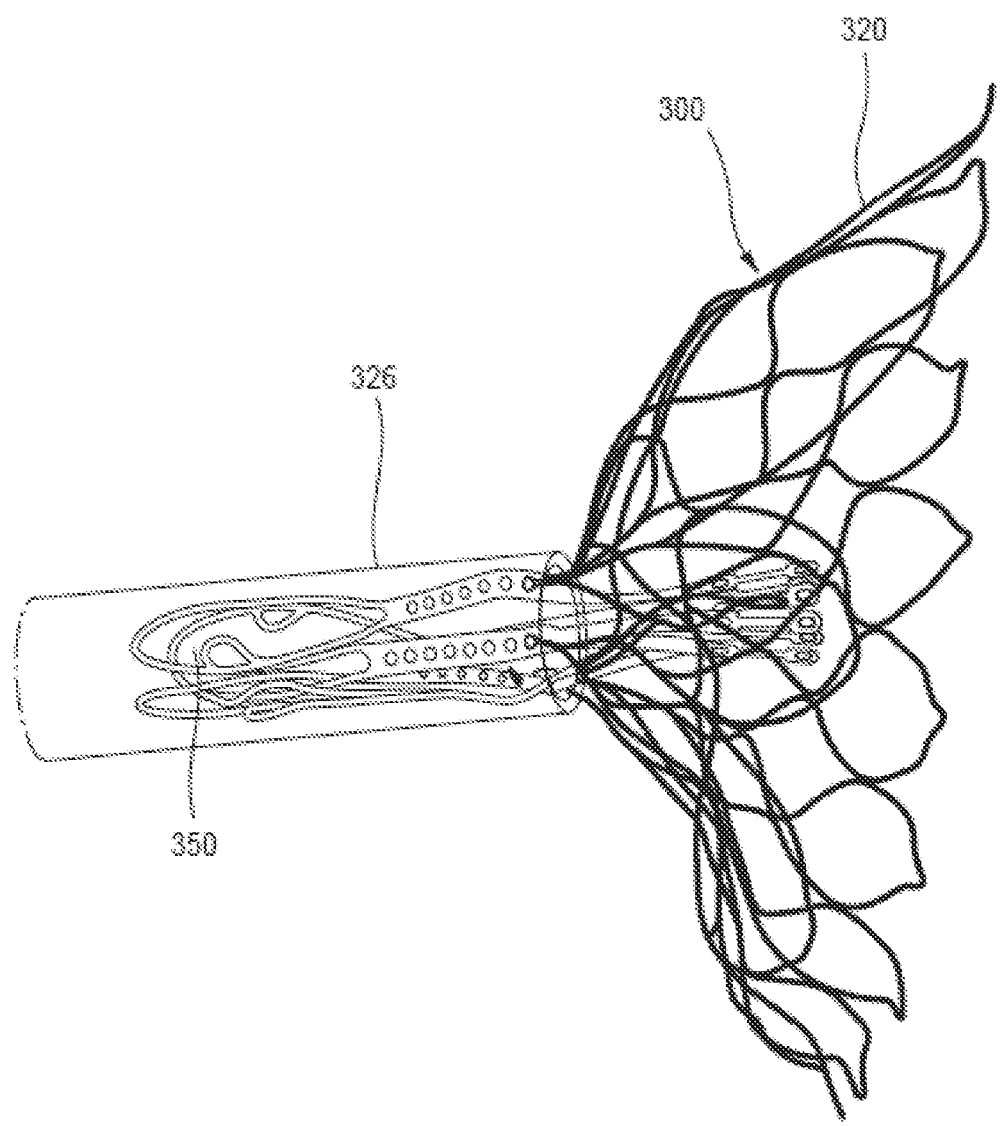
FIG. 20 is a side view of the assembly of FIG. 17 shown in a third partially deployed configuration in which the inverted outer frame is substantially deployed outside of the delivery sheath.
Figure 21:
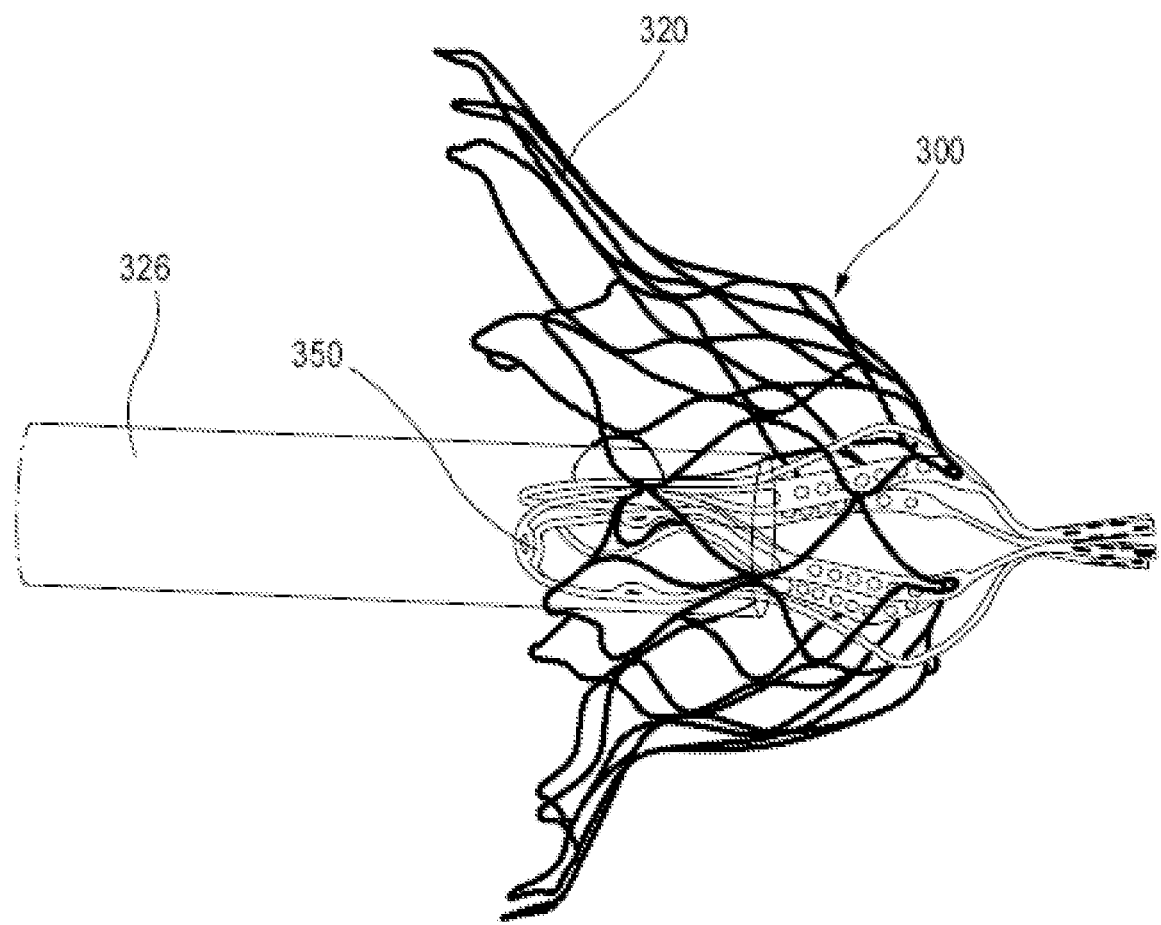
FIG. 21 is a side view of the assembly of FIG. 17 shown in a fourth partially deployed configuration in which the outer frame has reverted and assumed a biased expanded configuration.

As the valve 300 exits the lumen of the delivery sheath 326, the outer frame assembly 310 exits first in its inverted configuration as shown in the progression of FIGS. 18-20 (see also FIG. 22). After the outer frame assembly 310 is fully outside of the lumen of the delivery sheath 326, the outer frame 320 can revert to its expanded or deployed configuration as shown in FIGS. 21, 23 and 24. In some embodiments, the outer frame 320 can revert automatically after fully exiting the lumen of the delivery sheath due to its shape-memory properties. In some embodiments, a component of the delivery sheath or another device can be used to aid in the reversion of the outer frame assembly 310. In some embodiments, the pusher device and/or the tether can be used to aid in the reversion of the outer frame assembly 310. The valve 300 can continue to be deployed until the inner frame 350 is fully deployed with the left atrium and the valve 300 is in the expanded or deployed configuration (as shown, e.g., in FIGS. 15 and 24). The valve 300 and the tether 336 can then be secured to the apex of the heart with an epicardial pad device 339 as shown in FIG. 24 and as described in more detail in the '572 PCT application and the '305 PCT application.

Figure 25:
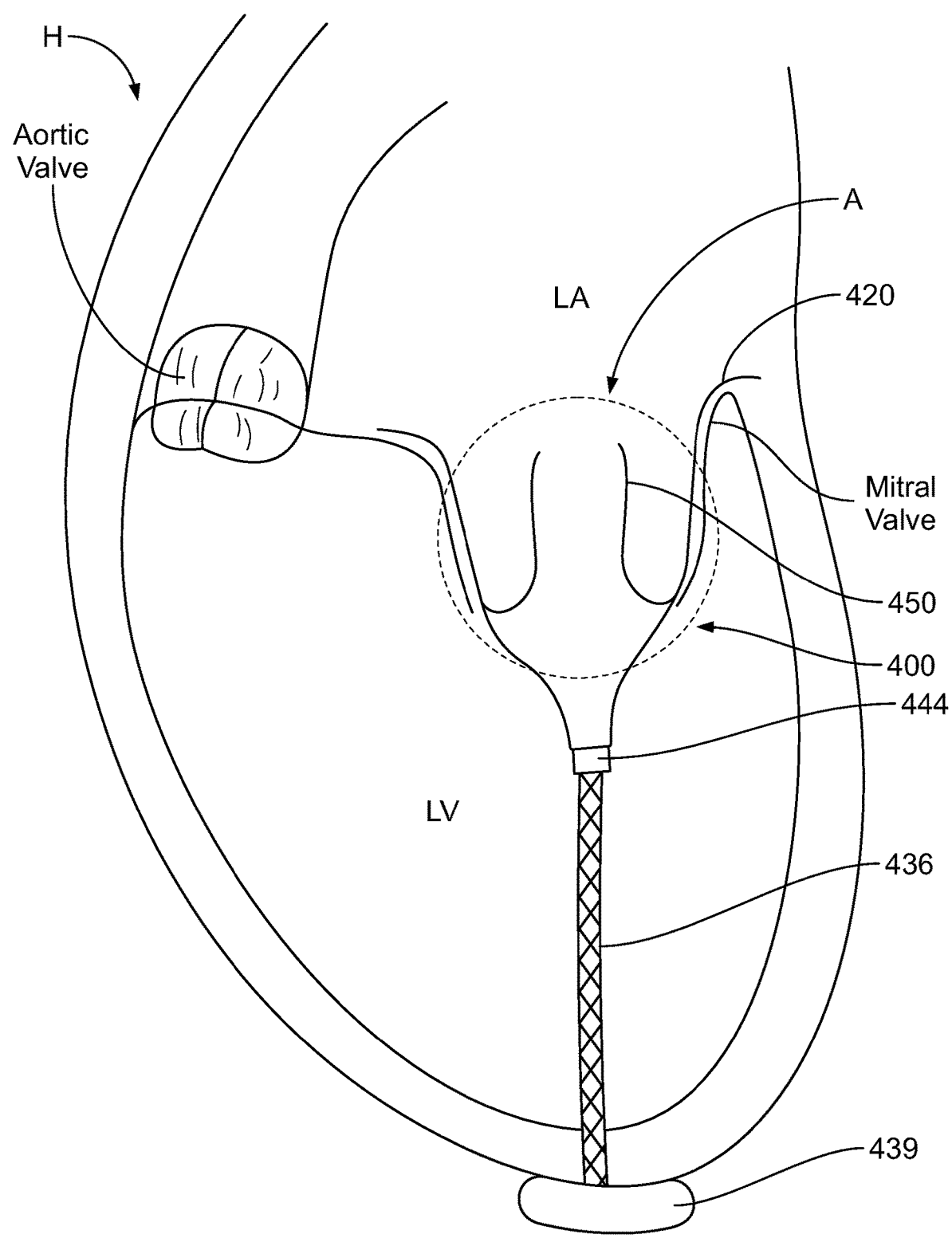
FIG. 25 is an illustration of an embodiment of a prosthetic heart valve shown disposed within a portion of a heart.
Figure 26:
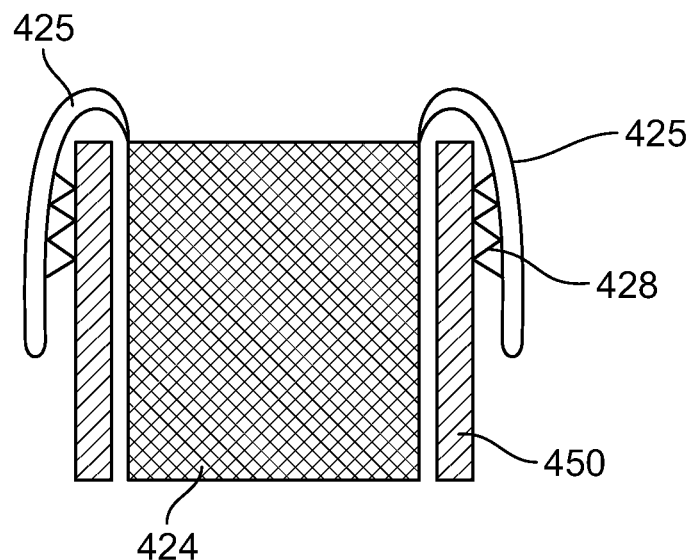
FIG. 26 is a side view of a portion of the prosthetic heart valve of FIG. 25 with a secondary valve apparatus coupled thereto with clips on an atrium portion of the prosthetic heart valve.
Figure 27:
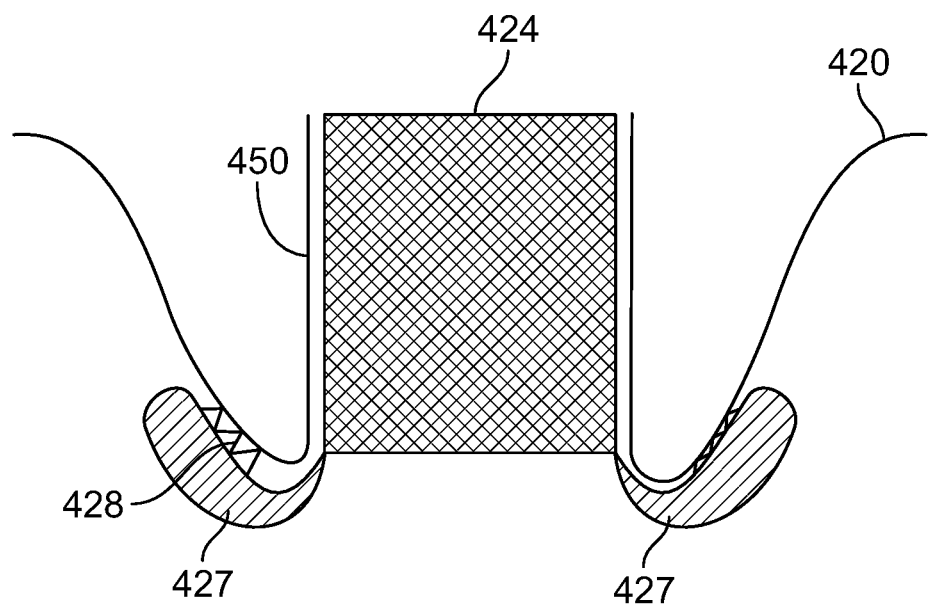
FIG. 27 is a side view of a portion of the prosthetic heart valve of FIG. 25 with a secondary valve apparatus coupled thereto with clips on a ventricle portion of the prosthetic heart valve.

As described above, some prosthetic heart valves, such as the prosthetic heart valve described above, can be prone to wear over time and valve function can then be slowly compromised. In such a case, a secondary valve apparatus can be deployed within and/or attached to, the previously implanted worn prosthetic valve. FIG. 25 illustrates a portion of a heart with a prosthetic mitral valve 400 implanted within a native mitral valve annulus. The valve 400 includes an outer frame 420, an inner frame 450, and leaflets (not shown) disposed within the inner frame 450. The valve 400 may be similar or identical to other valves described above, such as valve 300. A tether 436 is coupled to the inner frame 450 at a connecting portion 444 and secured to a wall of the heart with an epicardial pad device 439. Other features (e.g., coverings, etc.) of the valve 400 are not shown for ease of illustration. FIG. 26 illustrates a secondary valve apparatus 424 deployed within the inner frame 450 and leaflets (not shown) of the valve 400 and clipped to an atrial end portion of the inner frame 450 with clips 425. FIG. 27 illustrates the secondary valve apparatus 424 deployed within the inner frame 450 and leaflets (not shown) and clipped to the outer frame 420 at a ventricular end portion of the valve 400 with clips 427. The secondary valve apparatus 424 can include a frame with leaflets (not shown) to provide a new valve to function in place of the existing valve 400. The secondary valve apparatus 424 can also include other features such as, for example, coverings on one or both sides of the frame.

In some embodiments, the frame of the secondary valve apparatus 424 can be formed with a self-expanding material, such as nitinol, such that the secondary valve apparatus 424 can be compressed for delivery via a delivery catheter and when deployed can expand to a biased expanded configuration within the inner frame 450. In some embodiments, the secondary valve apparatus 424 can be formed of a material that can be expanded using an expansion device such as a balloon. The secondary valve apparatus 424 can include a combination of radial force applied upon the inner frame 450 and the clips 425, 427 that interact with the existing implanted valve 400 to lock the secondary valve apparatus 424 into position and prevent embolization from the existing valve 400.

In some embodiments, the clips 425, 427 can have controlled actuation that allows for positioning of the secondary valve apparatus 424 and clips 425, 427 multiple times to achieve an optimal positioning. In other words, the clips 425, 427 can be actuated and re-actuated as needed. In some embodiments, the clips 425, 427 can be independently actuated. In some embodiments, the clips 425, 427 can be actuated simultaneously.

In some embodiments, the clips 425, 427 can include a textured surface 428 that can engage or contact the inner frame 450 to provide additional holding force. In some embodiments, the clips 425, 427 can be anchored directly to an outside of the inner valve assembly. In some embodiments, the clips 425, 427 can anchor to, for example, a covering (not shown) disposed on the inner frame 450 or outer frame 420 (e.g., 230, 232 described above). In some embodiments, the clips 425, 427 can be anchored to a pocket covering (not shown) extending between a portion of the inner frame 450 and a portion of the outer frame 420. In some embodiments, the clips 425, 427 can be anchored to the leaflets (not shown) of the valve 400 or any other portion of the valve 400.

In the embodiment of valve 400 having an anchoring tether 436, the secondary valve apparatus 424 and clips 425, 427 can be delivered transseptally. For implantation within an existing valve that does not include an anchoring tether, the secondary valve apparatus 424 and clips 425, 427 can be delivered transapically or transseptally. The secondary valve apparatus 424 can be delivered with, for example, a delivery catheter, and can be formed with a material that allows it to be compressed within the delivery catheter, and then can self-expand to a biased expanded configuration when moved outside of the delivery catheter. In some embodiments, the secondary valve apparatus 424 can be formed with an expandable material that can be expanded within the inner frame 450 using, for example, a balloon catheter.

Figure 28:
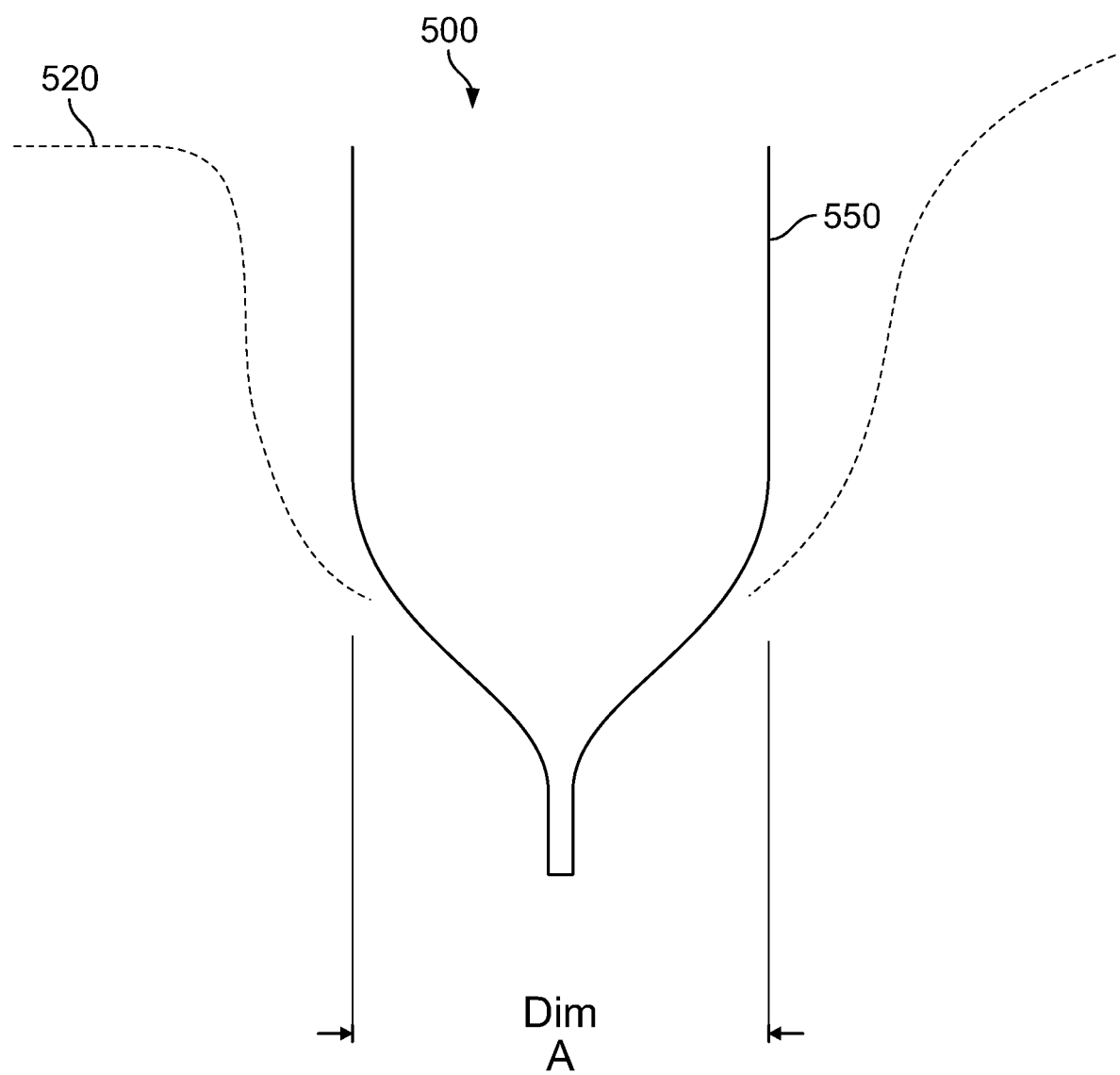
FIG. 28 is a schematic illustration of a portion of a prosthetic heart valve in a first configuration having a first inner diameter.
Figure 29:
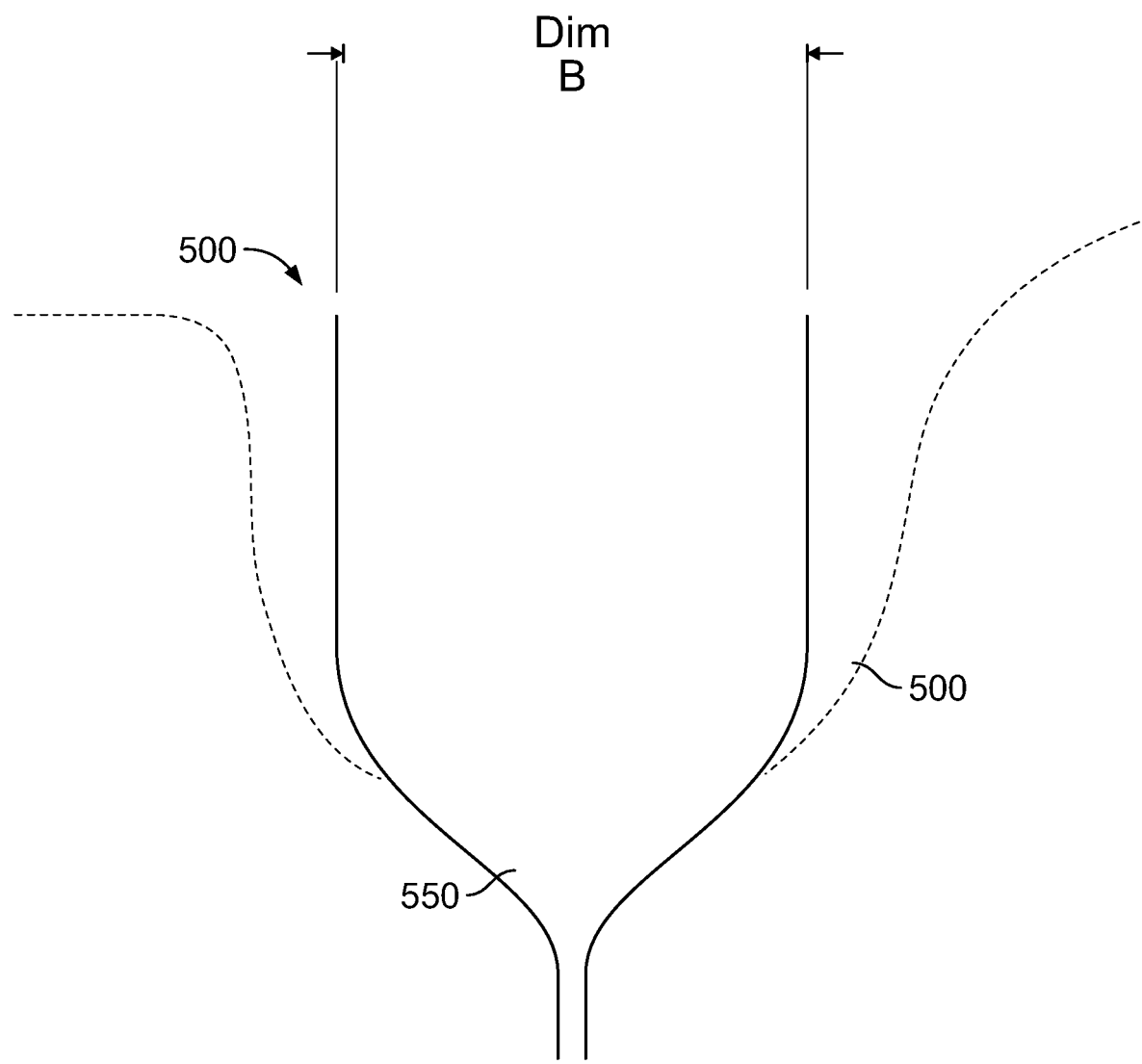
FIG. 29 is a schematic illustration of the portion of a prosthetic heart valve of FIG. 28 in a second configuration having a second larger diameter.

As described above, prior to deploying the secondary valve 424 within the inner frame 450, the inner frame 450 may need to be expanded to provide space for the insertion of the secondary valve apparatus 424. Further, if the existing leaflets of the valve 400 have become stenotic, the existing leaflets can be opened with the expansion device. FIGS. 28 and 29 illustrate a prosthetic heart valve 500 including an outer frame 520 and an inner frame 550 and the change in inner diameter of the inner frame 550 from expansion with a balloon expansion device. As shown in FIG. 28, prior to expansion with a balloon expansion device, the inner frame 550 has an inner diameter of dimension A and as shown in FIG. 29, the inner frame 550 has an inner diameter of dimension B after expansion that is larger than dimension A. FIGS. 30-33 illustrate two example expansion devices that can be used to expand, for example, an inner frame of a valve prior to implantation of a secondary valve apparatus.

Figure 30:
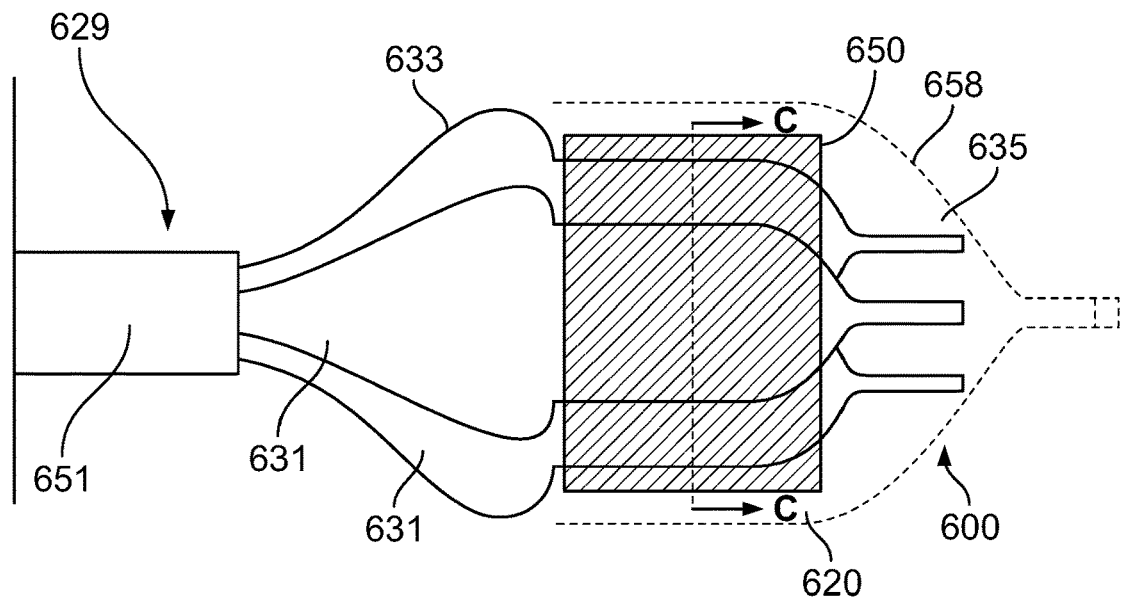
FIG. 30 is a side view of a portion of a prosthetic heart valve and a portion of a balloon expansion device, according to an embodiment.
Figure 31:
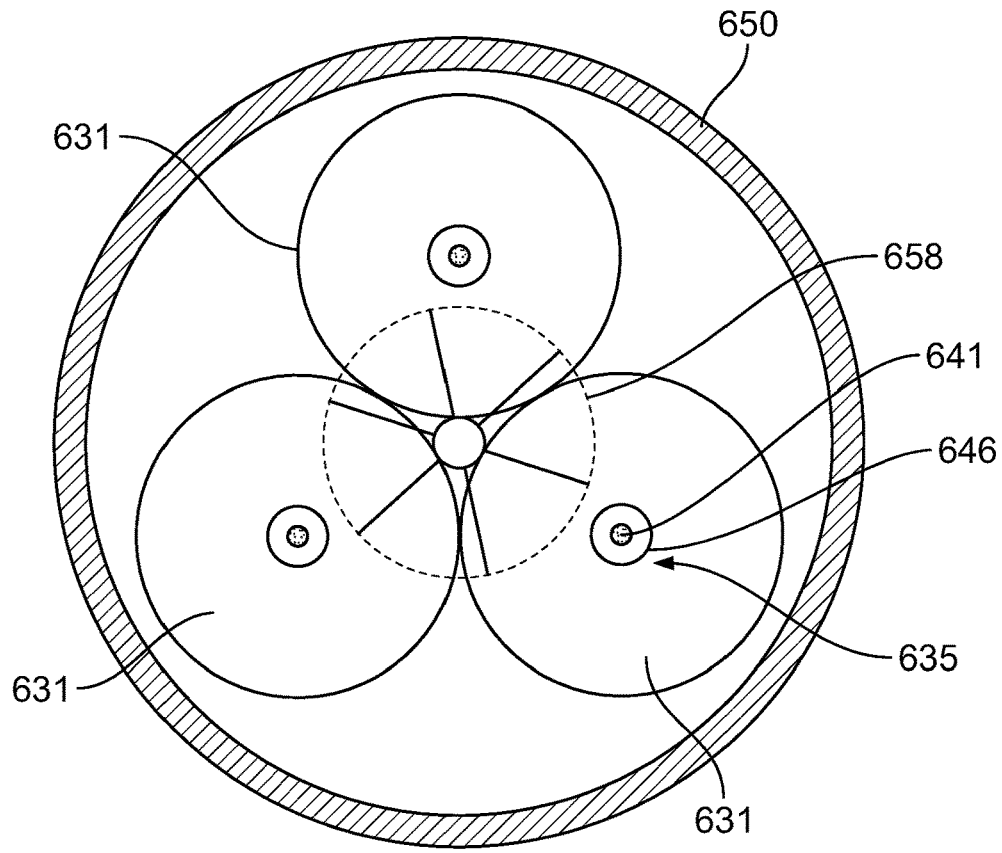
FIG. 31 is a cross-sectional view of the portion of a prosthetic heart valve and balloon expansion device of FIG. 30 taken along line C-C in FIG. 30.

FIG. 30 is a side view illustrating a portion of a balloon expansion device 629 disposed within a prosthetic heart valve 600 and FIG. 31 is a cross-sectional view taken along line C-C in FIG. 30. Prosthetic heart valve 600 may include an outer frame 620 and an inner frame 650, and may be similar or identical to other valves described herein, such as valve 300. As shown in FIGS. 30 and 31, in this embodiment, the balloon expansion device 629 includes three balloons 631 that can be delivered with a delivery catheter 651. Although not shown, the balloon expansion device 629 can include an elongate member that is coupled to an expansion medium such that a volume of the expansion medium can be communicated to the balloons 631 after being disposed within an interior of the valve 600. The balloons 631 include a distal tip portion 635 and a proximal portion 633. The proximal portion 633 has an enlarged diameter when expanded such that the balloons 633 are prevented from being inserted too far into the valve 600. As shown in FIG. 31, the balloons 631 can each include a guidewire lumen 646 through which a guidewire 641 can be slidably disposed and used to guide the insertion of the balloons 631 into the valve 600. The guidewire lumens 646 are offset from a centerline of the delivery catheter 651 used to deliver the balloon expansion device 629. Although balloons 631 are shown with a round or circular cross-section, in alternative embodiments, the balloons 631 can have a different cross-section, such as, for example, hemispherical. In some embodiments, the balloons can have a three-sided or triangular cross-section with one side being circular. In some embodiments, the balloons 631 may include more than three balloons.

A ventricle portion 658 (shown in dashed line in FIG. 31) of the valve 600 can include portions of the valve 600 that could interfere with the insertion of an expansion device to expand the inner frame 650 to prepare the inner frame 650 for insertion of a secondary valve apparatus. Thus, the use of multiple separate balloons 631 with narrow distal tip portions 635, allows for each of the balloons 631 to be inserted into a smaller space within the valve 600 without interfering with the ventricular components. The balloons 631 can be inserted in a collapsed configuration and when disposed in a desired position, can be expanded to expand the inner diameter of the inner frame 650. A secondary valve apparatus (not shown in FIGS. 30 and 31) as described herein can then be deployed within the inner frame 650. The ventricle portion 658 may include structures similar to those shown and described in connection with valve 200, such as a tether connection portion similar to tether connection portion 244. The density of structures in that area may make it otherwise difficult or impossible to pass a typical single large balloon within the valve prior to expansion.

Figure 32:
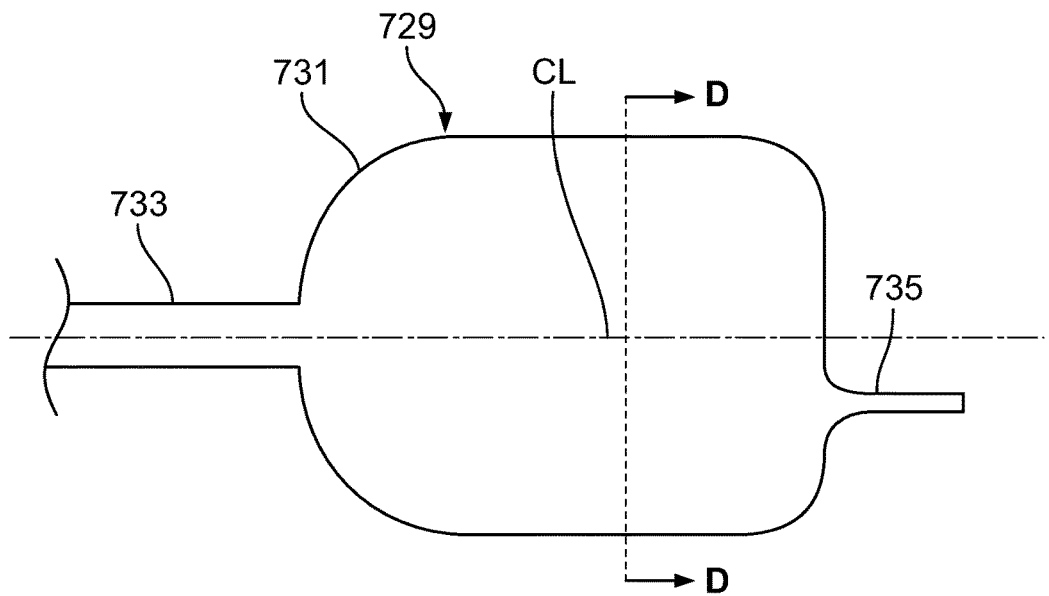
FIG. 32 is a side view of a portion of a balloon expansion device, according to another embodiment.
Figure 33:
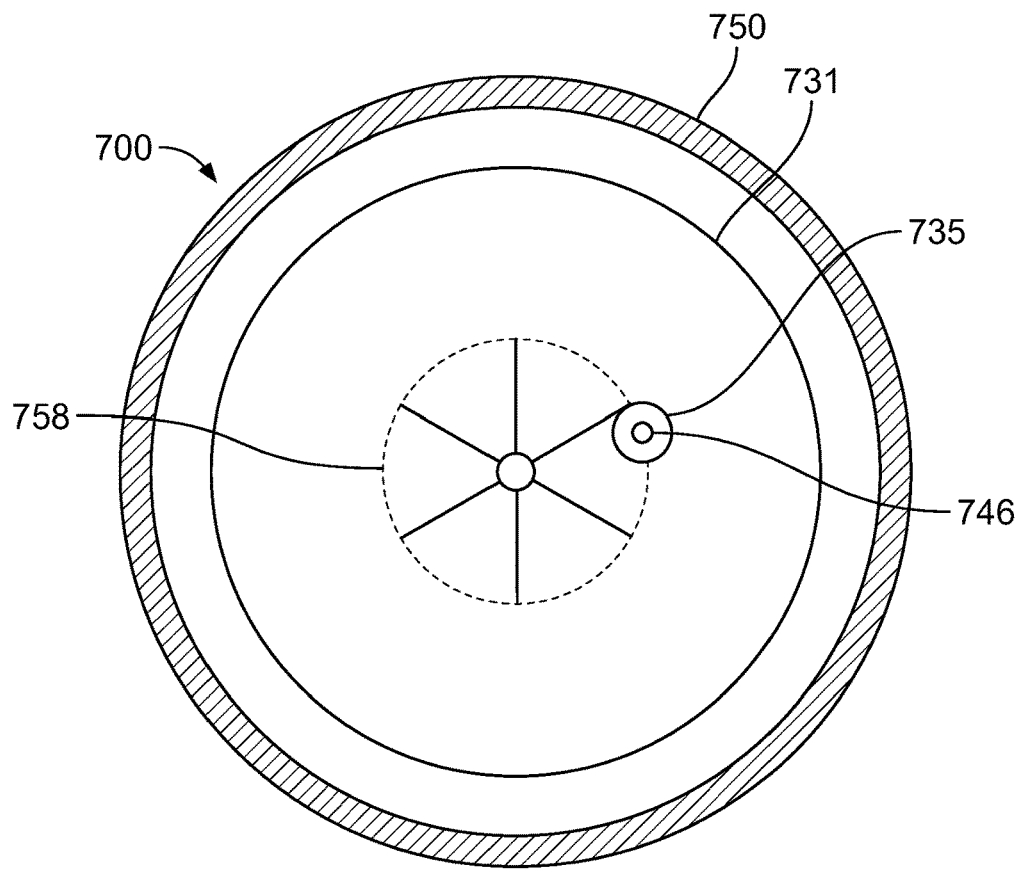
FIG. 33 is a cross-sectional view of the portion of a balloon expansion device of FIG. 32 taken along line D-D in FIG. 32 shown disposed within a cross-sectional top view of a portion of a prosthetic heart valve.

FIGS. 32 and 33 illustrate another embodiment of a balloon expansion device that can be used to expand a prosthetic heart valve to enlarge the inner diameter such that it can receive a secondary valve apparatus therein. FIG. 32 is a side view illustrating a portion of a balloon expansion device 729 and FIG. 33 is a cross-sectional view of the expansion device 729 taken along line D-D in FIG. 32 and shown disposed within a cross-sectional top view of a valve frame 750. Valve frame 750 may be similar or identical to any of the inner frames described above, and may be part of a valve 700 similar or identical to any of those described above. As shown in FIGS. 32 and 33, in this embodiment, the balloon expansion device 729 includes a single balloon 731 that can be delivered with a delivery catheter (not shown). The balloon expansion device 729 can include an elongate member (not shown) that is coupled to an expansion medium such that a volume of the expansion medium can be communicated to the balloon 731 after being disposed within an interior of the valve frame 750. The balloon 731 includes a distal tip portion 735 and a proximal portion 733. The balloon 731 can include a guidewire lumen 746 through which a guidewire (not shown) can be slidably disposed and used to guide the insertion of the balloon 731 into the valve frame 750. The distal tip portion 735 and guidewire lumen 746 are offset from a centerline CL of the balloon 731. As described for balloons 631, balloon 731 can have a round or circular cross-section as shown, or can have a different cross-section, such as, for example, hemispherical. In some embodiments, the balloon 731 can have a three-sided or triangular cross-section with one side being circular.

As described above for the previous embodiment, a ventricle portion 758 (shown in FIG. 33) of the valve 700 can include portions of the valve 700 that could interfere with the insertion of the expansion device 700 to expand the valve frame 750 to prepare the valve frame 750 for insertion of a secondary valve apparatus. Thus, the offset positon of the narrow distal tip portion 735 of balloon 731 allows for the balloon 731 to be inserted within the valve frame 750 without interfering with the ventricular components, which are most dense near a centerline of the valve frame 750. The balloon 731 can be inserted in a collapsed configuration and when disposed in a desired position, can be expanded to expand the inner diameter of the valve frame 750. A secondary valve apparatus (not shown in FIGS. 32 and 33) as described herein can then be deployed within the valve frame 750.

The balloon expansion devices 629, 729 can be configured to expand the inner diameter of a portion of an existing implanted prosthetic heart valve that is self-expanding, such as a valve formed with a material such as nitinol, or a valve that is formed with a material that is designed to be balloon expanded. For example, in some embodiments, the previously or first implanted valve can be formed at least partially with a plastically deformable material, such as, for example, stainless steel or cobalt chromium.

As described previously, in some embodiments, all or a portion of the valve frame can be formed at least in part with a material that is not plastically deformable, such as nitinol, but include breakaway regions to allow the valve to be modified. The breakaway regions can be formed, for example, with a material such as stainless steel or cobalt chromium. Similarly, a breakaway region can be of reduced dimension, creating a thin, frangible location which fractures and thus allows for frame expansion. In some embodiments, having a valve frame formed with a material that is not plastically deformable, the valve could include a locking mechanism to lock the valve into the deformed shape upon expansion. In some embodiments, it may be desired to have hinged frame elements to facilitate expansion or locking.

Figure 34:
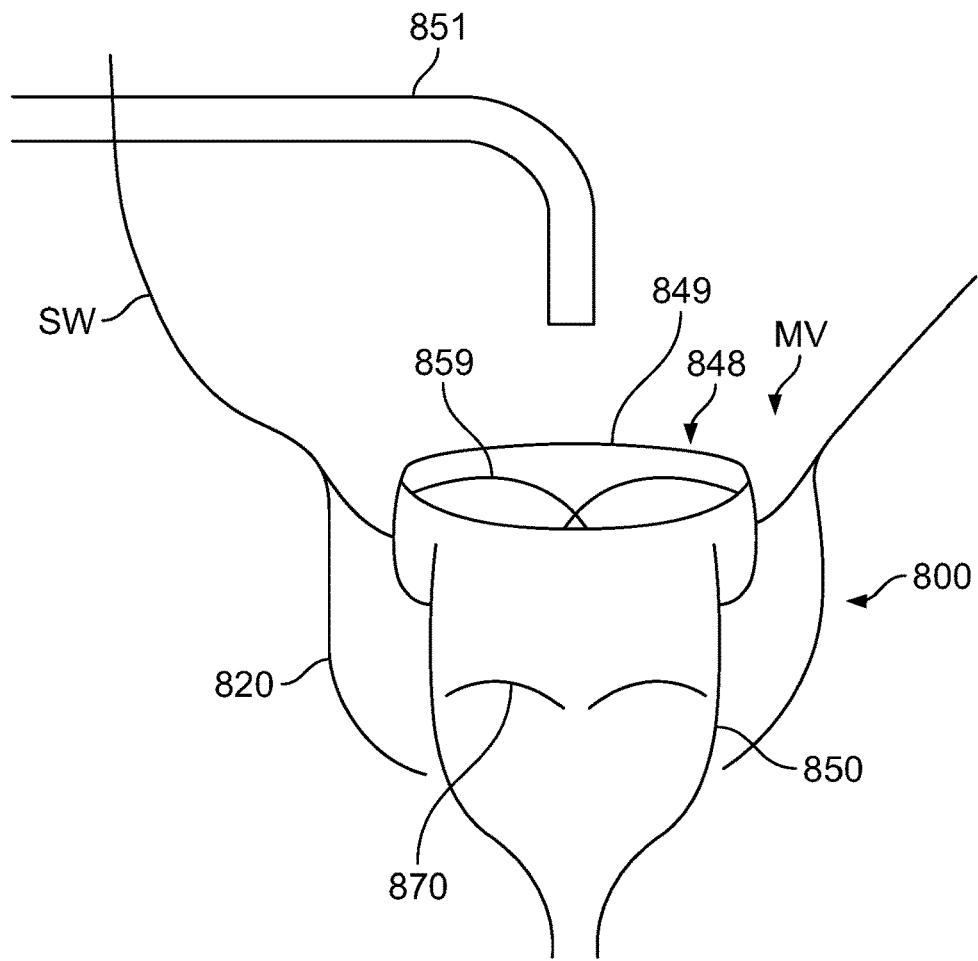
FIG. 34 is a schematic illustration of a prosthetic heart valve shown disposed within a portion of a heart, and a secondary valve apparatus coupled to the prosthetic heart valve.
Figure 35:
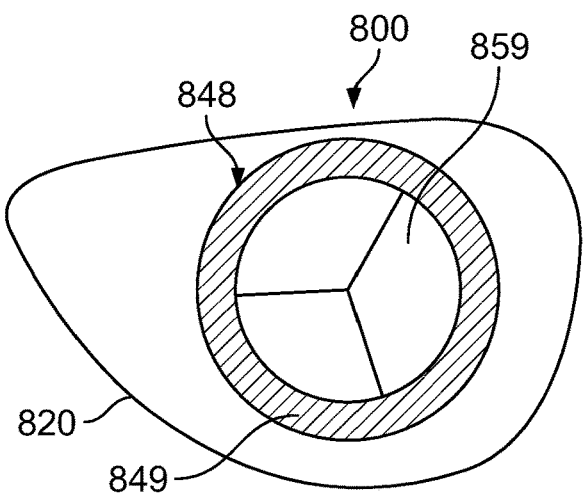
FIG. 35 is a top view of the prosthetic heart valve and secondary valve apparatus of FIG. 34.

FIGS. 34 and 35 illustrate another embodiment of a secondary valve apparatus that can be deployed within or coupled to a worn or failing existing implanted prosthetic heart valve. FIG. 34 illustrates a prosthetic heart valve 800 disposed within, offset in relation to, or in series with, a mitral valve MV and that includes an outer frame 820, an inner frame 850 and leaflets 870. Valve 800 may be similar or identical to any of the other valves described herein. A secondary valve apparatus 848 is coupled to an atrium end portion of the inner frame 850. In this embodiment, the secondary valve apparatus 848 includes a cap portion 849 with valve leaflets 859 disposed within an interior of the cap portion 849. The secondary valve apparatus 848 can be delivered transseptally through a septal wall SW using a delivery catheter 851. The secondary valve apparatus 848 can be secured to the atrium end portion of the inner frame 850 of the existing valve 800 with one or more coupling components, such as, for example, barbs, hooks or anchors. As shown in FIG. 34, the secondary valve apparatus 848 may be positioned in series with (or offset in relation to) the existing valve 800, such that prosthetic leaflets 870 are still free to move, although the new prosthetic leaflets 859 are expected to provide the valve functionality, as the existing prosthetic leaflets 870 may no longer be functioning acceptably. In alternative embodiments, the secondary valve apparatus 848 can be secured to an atrium end portion of the outer frame 820, or another portion of the valve 800, such as a pocket covering between the inner frame 850 and the outer frame 820. The secondary valve apparatus 848 provides a new valve (e.g., leaflets) to function in place of the existing leaflets. If the existing leaflets 870 have become stenotic, the valve 800 can be expanded with a balloon expansion device to open the leaflets 870 prior to coupling the secondary valve apparatus 848 to the valve 800.

Figure 36:
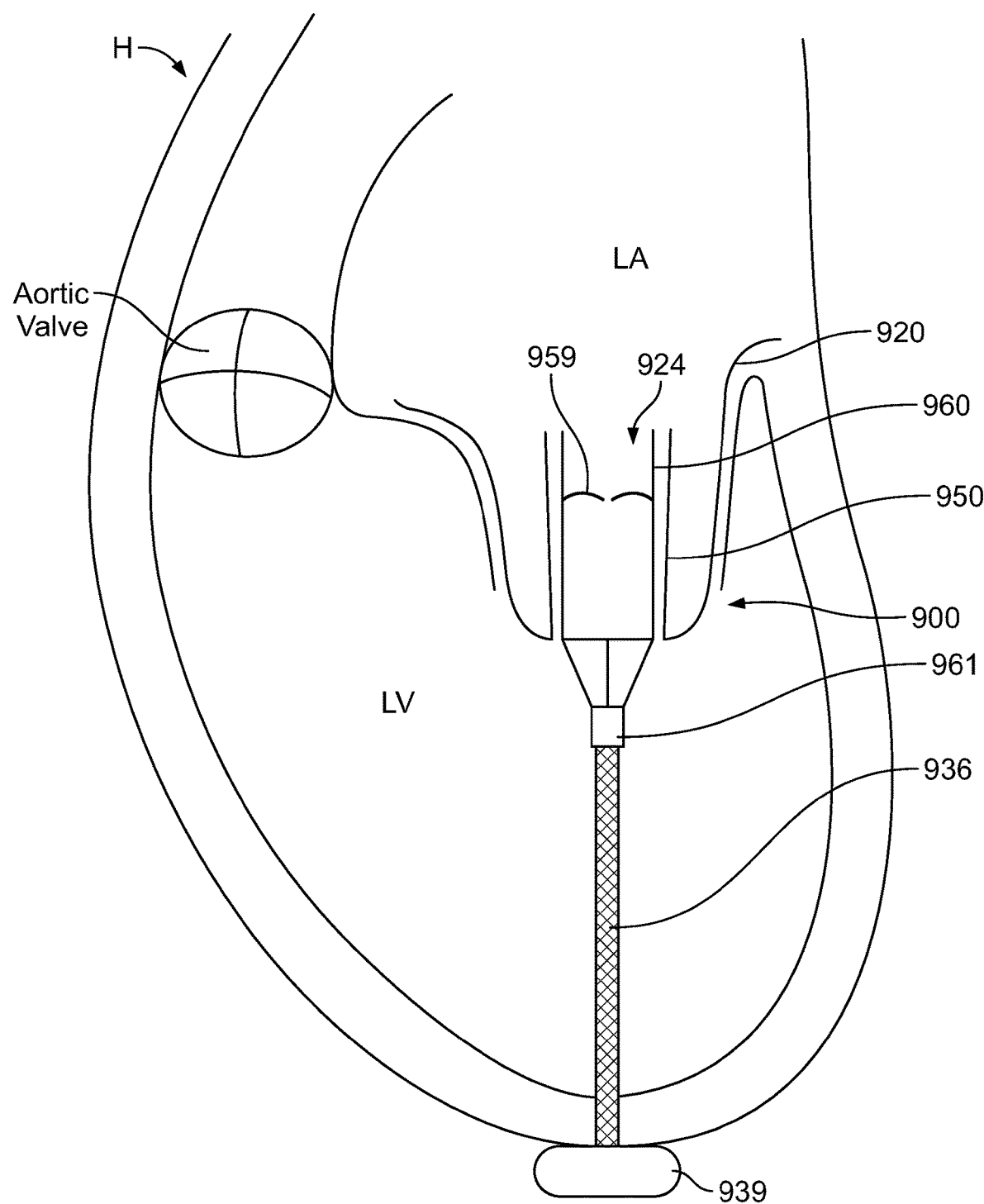
FIG. 36 is an illustration of an embodiment of a prosthetic heart valve shown disposed within a portion of a heart and a secondary valve apparatus disposed within the prosthetic heart valve.

FIG. 36 illustrates a prosthetic heart valve 900 shown disposed within a native mitral valve between the left atrium LA and left ventricle LV in heart H, and a secondary valve apparatus 924, according to another embodiment. In this embodiment, the existing implanted prosthetic heart valve 900 does not include a tether (e.g., tether 136, 436) to secure the position of the valve 900, although valve 900 may include similar features to those described above in connection with other valves, such as an inner frame 950 and outer frame 920. In this embodiment, the secondary valve apparatus 924 includes a frame 960 with valve leaflets 959 disposed therein and a tether 936 attached to a tether connecting portion 961 at a ventricle portion of the frame 960. The secondary valve apparatus 924 can also include other features not shown, such as coverings on the frame 960. In some embodiments, the secondary valve apparatus 924 can include an atrial cuff portion (not shown) similar to cuff portion 273 described above for prosthetic heart valve 200, to assist in anchoring the secondary valve apparatus 924.

The tether 936 can be secured to a wall of the heart with an anchoring device 939 (e.g., epicardial pad) in a similar manner as described above for previous embodiments, to secure the position of the secondary valve apparatus 924 within the heart, provide support to the ventricle of the heart, and stabilize the unstable or worn existing valve 900. In some embodiments, the tether 936 can be secured to a ventricle end portion of the frame 960 with a compression fit as described above for valve 200.

The secondary valve apparatus 924 can be delivered to the heart percutaneously with an apical or transseptal delivery approach. For example, the secondary valve apparatus 924 can be delivered transseptally using a delivery catheter in a similar manner as described above with respect to valve 300 and FIGS. 22-24. The secondary valve apparatus 924 can also be delivered semi-percutaneously or surgically.

As described for previous embodiments, the secondary valve apparatus 924 can be deployed within an interior of the existing implanted prosthetic heart valve 900 to replace the valve functions of the prosthetic heart valve 900. If necessary, a balloon expansion device can be used to expand the diameter of the valve 900 to provide space for the secondary valve apparatus 924, as described herein for other embodiments. The secondary valve apparatus 924 can be placed in a delivery catheter in a collapsed configuration and can be expanded or expandable during or after being deployed within the existing valve 900. For example, the frame 960 can be formed with an expandable material such that it can be expanded when deployed (e.g., with a balloon expansion device), or can be formed with a self-expanding material such that it can expand upon release from the delivery catheter. While tether 936 may assist in preventing the secondary valve apparatus 924 from migrating into the left atrium LA, frictional forces between frame 960 and components of prosthetic heart valve 900, such as inner frame 950, may assist the secondary valve apparatus 924 from migrating into the left ventricle LV. In addition or alternatively, portions of the secondary valve apparatus 924, such as frame 960, may include hooks, barbs, or other mechanisms in order to secure to components of prosthetic heart valve 900, such as inner frame 950, to assist in preventing migration of the secondary valve apparatus 924 into the left ventricle LV.

Figure 37:
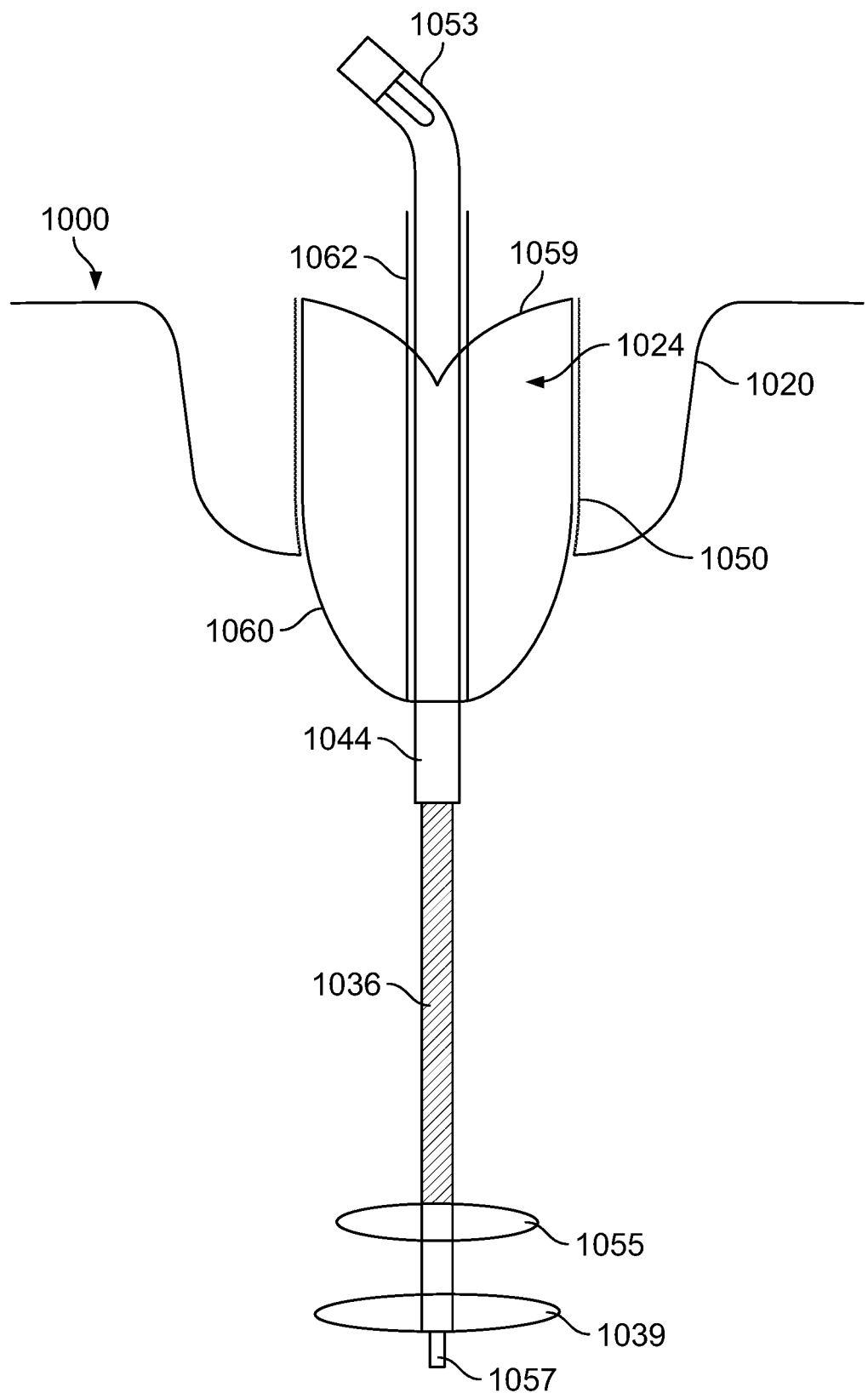
FIG. 37 is an illustration of a prosthetic heart valve shown disposed within a portion of a heart and another embodiment of a secondary valve apparatus disposed within the prosthetic heart valve.

FIG. 37 illustrates a prosthetic heart valve 1000 shown disposed within a native mitral valve between the left atrium and the left ventricle in the heart, and a secondary valve apparatus 1024, according to another embodiment. In this embodiment, the existing implanted prosthetic heart valve 1000 does not include a tether (e.g., tether 136, 436) to secure the position of the valve 1000, although valve 1000 may include similar features to those described above in connection with other valves, such as an inner frame 1050 and outer frame 1020. In this embodiment, the secondary valve apparatus 1024 includes a frame 1060 with valve leaflets 1059 disposed therein and a tether 1036 attached to the frame 1060. The secondary valve apparatus 1024 can also include other features not shown, such as coverings on the frame 1060. In some embodiments, the secondary valve apparatus 1024 can include an atrial cuff portion (not shown) similar to cuff portion 273 described above for prosthetic heart valve 200, to assist in anchoring the secondary valve apparatus 1024.

Figure 38:
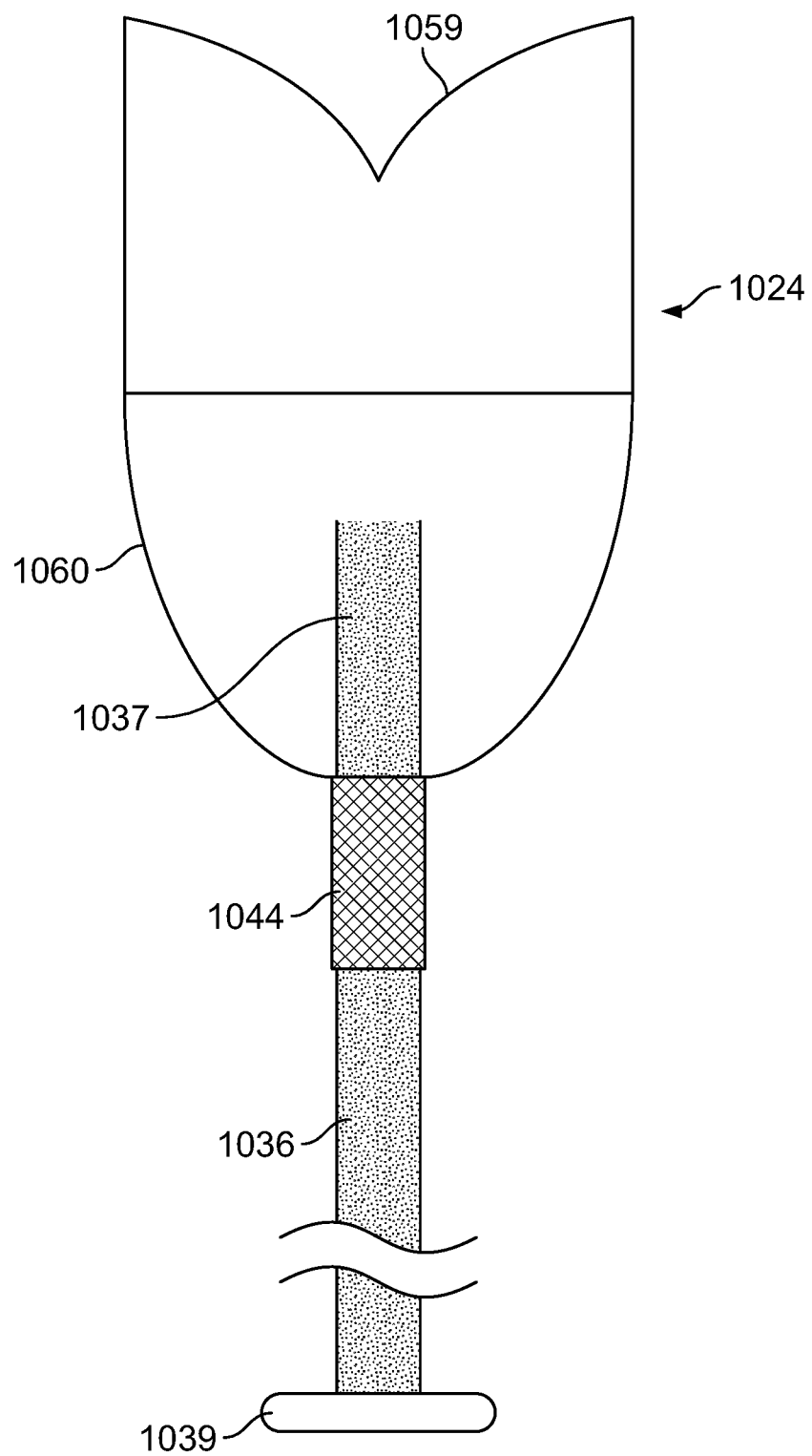
FIG. 38 is an isolated illustration of the secondary valve apparatus of FIG. 37 in a stage of implantation.
Figure 39:
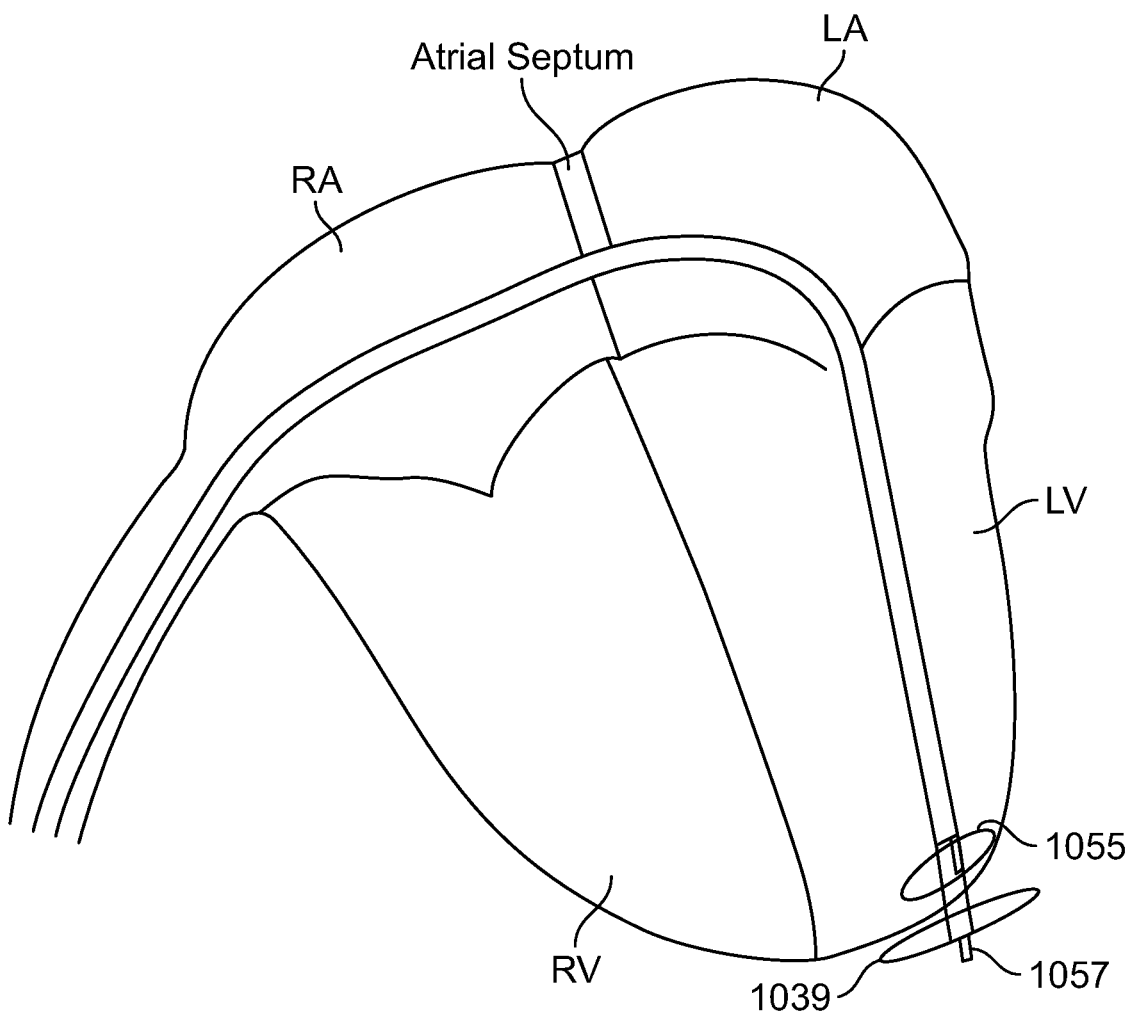
FIG. 39 is an illustration of the secondary valve apparatus of FIG. 37 in a different state of implantation than shown in FIG. 38.

Although secondary valve apparatus 1024 may be substantially similar or identical to secondary valve apparatus 924 in certain respects, it may include additional features. For example, although secondary valve apparatus 1024 may include an anchoring device 1039 that may be generally similar to anchoring device 939, it may also include an interior anchor device 1055 positioned a spaced distance from anchoring device 1039. In use, while anchoring device 1039 may be configured to be positioned on the epicardial surface of the left ventricle, interior anchor device 1055 may be configured to be positioned on the interior surface of the left ventricle, the two anchor devices effectively sandwiching the ventricular wall therebetween, as can be seen in FIG. 39. It should be understood that the interior anchor device 1055 may be omitted in certain embodiments, and is omitted from FIGS. 38 and 40.

Figure 40:
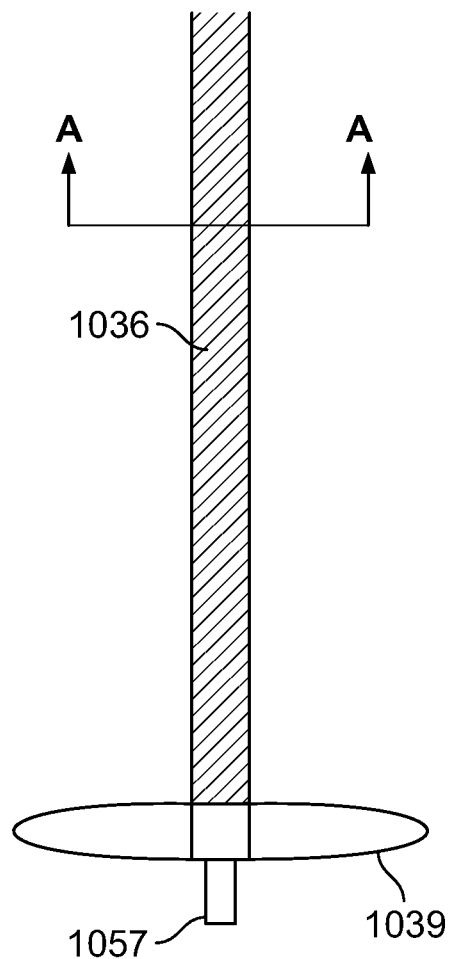
FIG. 40 is an illustration of a tether of the secondary valve apparatus of FIG. 37.
Figure 41:
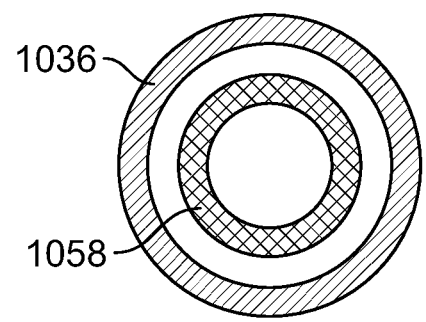
FIG. 41 is cross section of the tether of the secondary valve apparatus taken along the line A-A of FIG. 40.

Referring to FIGS. 40-41, another additional feature of secondary valve apparatus 1024 may be that the tether 1036 includes a lumen through which a microcatheter 1058 is disposed. For example, FIG. 41 illustrates a cross-section of the tether 1036 along line A-A of FIG. 40. Tether 1036 may be formed of a relatively soft material, such as a braided fiber. As shown in FIG. 41, tether 1036 may include a lumen through which the microcatheter 1058 is disposed, with a tip 1057 of the microcatheter 1058 visible in FIG. 40. The microcatheter 1058 may be formed of a more rigid material than the braided fiber of tether 1036, which may for example be a metal, metal alloy, or plastic material.

Referring now to FIG. 39, securing anchoring device 1039 and interior anchor device 1055 to the wall of the left ventricle LV is illustrated schematically, with the previously-implanted prosthetic heart valve 1000 omitted from the drawing for clarity of illustration. The left ventricle LV may be accessed transseptally as described elsewhere herein, with the microcatheter tip 1057 passing into or through the ventricular apex. The microcatheter tip 1057 may serve as an entryway for material to pass into the lumen of the microcatheter 1058 from the surrounding anatomy, or for material to pass through the microcatheter 1058 to be expelled into the surrounding anatomy. For example, in some instances, it may be beneficial to remove some amount of blood from the pericardium during the delivery procedure, which blood may be removed via the microcatheter 1058. It may also be beneficial to inflate the pericardium some amount to create extra space for receiving an anchor, and particularly an expandable anchor, such as anchoring device 1039. The microcatheter 1058 may allow for fluid to be delivered into the pericardium for the above-described inflation. Surgical sealants and/or plugs may also be deployed into and/or through the microcatheter 1058 at or near the completion of the procedure, for example to seal any exposed lumens of the microcatheter, or to otherwise assist in creating any additional seals near the tip 1057 of the microcatheter 1058. Still further, as noted above, microcatheter 1058 may be formed of a relatively rigid material, which may assist in providing overall rigidity to the tether 1036, which in turn may assist in the tether 1036 being used as a rail over which components may be delivered, such as portions of secondary valve apparatus 1024, described in greater detail below. Referring back to FIG. 37, the tether 1036 may include a rapid exchange port 1053 to assist in the delivery.

Referring again to FIG. 39, during a valve-in-valve procedure using secondary valve apparatus 1024, the tether 1036, anchoring device 1039, microcatheter 1058, and interior anchor device 1055 (if being used), may be delivered to the apex of the left ventricle LV in a transseptal manner. It is repeated here that FIG. 39 omits the previously implanted prosthetic heart valve 1000. However, it should be understood that the microcatheter structure may also be used when implanting a primary tethered prosthetic heart valve, such as one similar or identical to prosthetic mitral valve 200. In other words, although the microcatheter 1058 provides certain benefits described in connection with a valve-in-valve procedure, similar or identical benefits may be realized from the use of a microcatheter within a tether in connection with a primary prosthetic heart valve implantation procedure. In either event, if anchoring device 1039 is an expandable epicardial pad, it may be released from an overlying sheath of a delivery device or introducer device into the desired position, and allowed to expand into place. Interior anchor device 1055, if being used, may next be released from the delivery device on the interior of the left ventricle LV. Although interior anchor device 1055 may be expandable and have a structure generally similar to other anchors described herein, it need not be expandable and may be small enough to be delivered into place without requiring expansion.

It should be understood that both anchors 1039, 1055 are coupled to tether 1036, and a length of the tether 1036 may be released from an overlying delivery catheter by withdrawing the delivery catheter proximally. In other embodiments of prosthetic heart valves (whether a secondary valve apparatus or otherwise) described herein, a tether was fixed to the prosthetic heart valve, for example to an outer frame of the prosthetic heart valve, prior to delivery of the valve. In the present embodiment, however, the secondary valve apparatus 1024, and in particular the leaflets 1059 and the frame 1060, may be delivered over the tether 1036, with the tether 1036 acting as a rail to guide the leaflets 1059 and the frame 1060 toward the native mitral valve annulus to a desired position. For example, the frame 1060 of the secondary valve apparatus 1024 may be similar or identical to the inner frame 250 of prosthetic heart valve 200, and may include a tether connecting portion 1044 similar or identical to tether connecting portion 244, except that the tether connection portion 1044 is not translationally fixed to the tether 1036 during the delivery of the frame 1060. Rather, as shown in FIG. 37, the delivery catheter 1062 may be pulled proximally relative to the frame 1060 and leaflets 1059 of the secondary valve apparatus 1024 to allow the frame 1060 to expand within prosthetic heart valve 1000 (or otherwise to expand into the native mitral valve annulus if the procedure is a primary prosthetic heart valve implantation). If the procedure is a valve-in-valve procedure, a balloon may be used to expand the prosthetic heart valve 1000 as described in other embodiments above. Notably, while the secondary valve apparatus 1024 is expanded into place, a length of the tether may extend through and beyond the frame 1060 in a direction toward the left atrium LA.

At this stage in the delivery, frame 1060 and leaflets 1059 have expanded, but the tether 1036 has not been tensioned and the tether has not been securely fixed to the frame 1060. The delivery catheter 1062 may be advanced distally, through leaflets 1059, until it contacts a ventricular portion of the frame 1060, for example the tether connecting member 1044 or structures of the frame adjacent to the tether connecting member. In this position, the tether 1036 can be pulled proximally to tension the tether 1036 to a desired tension, with the distal end of the delivery catheter 1062 helping ensure that the frame 1060 does not move during the tensioning. When the desired tension of tether 1036 is achieved, the tether 1036 can be translationally fixed or locked to the tether connecting member 1044. For example, FIG. 38 illustrates secondary valve apparatus 1024 with the anatomy and the primary prosthetic heart valve 1000 (if the procedure is a valve-in-valve procedure) omitted. As can be seen, the tether 1036 extends into tether connecting portion 1044, with an excess length 1037 of the tether 1036 extending beyond the tether connecting portion 1044. The tether 1036 may be fixedly secured to the tether connecting portion 1044 in any suitable fashion. For example, the tether connection portion 1044 may include a locking pin which may be activated to pierce and pass through a portion of the tether 1036 to translationally lock the frame 1060 relative to the tether 1036. Other locking mechanisms may also be suitable. For example, if tether connecting portion 1044 includes collapsible micro-Vs as described in connection with prosthetic heart valve 200, the micro-Vs may be forced to collapse on the tether 1036 to crimp onto the tether 1036, for example by advancing a secondary device through the delivery catheter 1062 with features for collapsing the micro-Vs. Still other suitable mechanisms may be provided. For example, an interior of tether connection portion 1044 may include barbs or other features that allow for frame 1060 to be advanced in one direction along the tether 1036, but to restrict movement in the opposite direction.

Still referring to FIG. 38, once the frame 1060 is translationally locked to the tether 1036, for example via tether connection portion 1044, the excess length 1037 of the tether 1036 is preferably removed so as not to interfere with proper functioning of the secondary valve apparatus 1024. In one example, a cautery tool may be passed through the delivery catheter 1062 and over the tether 1036, and when the cautery tool is positioned on the tether 1036 adjacent the tether connecting portion 1044, the cautery tool may be activated to cauterize the tether 1036, causing the excess length 1037 of the tether 1036 to break away from the remaining portions of the tether 1036. The excess length 1037 of the tether 1036 may be removed through the delivery catheter 1062, and the remaining delivery instruments may be removed from the body to complete the procedure.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

In addition, the systems and methods described herein can also be adapted for use with a prosthetic tricuspid valve. For example, in such a case, a procedural catheter can be inserted into the right ventricle of the heart, and the delivery sheath delivered to the right atrium of the heart either directly (transatrial), or via, for example, the jugular or femoral vein to deliver a secondary valve apparatus as described herein.

According to a first aspect of the disclosure: a method of implanting a secondary prosthetic heart valve comprises:
delivering the secondary prosthetic heart valve to a vicinity of a native valve annulus, the native valve annulus having a primary prosthetic heart valve implanted therein, the primary prosthetic heart valve including a primary frame and a set of primary prosthetic leaflets, the secondary prosthetic heart valve being received within a delivery device in a collapsed condition during the delivering;
releasing the secondary prosthetic heart valve from the delivery device to allow the secondary prosthetic heart valve to transition to an expanded condition; and
coupling the secondary prosthetic heart valve to the primary prosthetic heart valve so that secondary prosthetic leaflets of the secondary prosthetic heart valve are positioned in series with (or offset in relation to) the primary prosthetic leaflets of the primary prosthetic heart valve, such that the secondary prosthetic leaflets are positioned a spaced distance from the primary prosthetic leaflets in a direction of blood flow through the primary prosthetic heart valve; and/or
the primary prosthetic heart valve is a prosthetic mitral valve or a prosthetic tricuspid valve, and the secondary prosthetic heart valve is positioned on an atrial side of the primary prosthetic heart valve in an upstream direction of blood flow through the primary prosthetic heart valve; and/or
the primary frame includes a primary inner frame to which the primary prosthetic leaflets are coupled, and a primary outer frame engaged with the native valve annulus; and/or
coupling the secondary prosthetic heart valve to the primary prosthetic heart valve includes engaging barbs, hooks, or anchors of the secondary prosthetic heart valve to the primary inner frame; and/or
coupling the secondary prosthetic heart valve to the primary prosthetic heart valve includes engaging barbs, hooks, or anchors of the secondary prosthetic heart valve to the primary outer frame; and/or
coupling the secondary prosthetic heart valve to the primary prosthetic heart valve includes engaging barbs, hooks, or anchors of the secondary prosthetic heart valve to a covering extending between the primary inner frame and the primary outer frame; and/or
expanding the primary leaflets with a balloon expansion device prior to coupling the secondary prosthetic heart valve to the primary prosthetic heart valve.

According to a second aspect of the disclosure, a method of implanting a secondary prosthetic heart valve in a heart of a patient comprises:
delivering the secondary prosthetic heart valve to a vicinity of a native valve annulus, the native valve annulus having a primary prosthetic heart valve implanted therein, the primary prosthetic heart valve including a primary outer frame engaged to the native valve annulus, a primary inner frame, a set of primary prosthetic leaflets coupled to the primary inner frame, and a tether having a first end coupled to the primary inner frame and a second end coupled to an anchor that is engaged to a surface of the heart, the secondary prosthetic heart valve being received within a delivery device in a collapsed condition during the delivering;
releasing the secondary prosthetic heart valve from the delivery device to allow the secondary prosthetic heart valve to transition to an expanded condition; and
coupling the secondary prosthetic heart valve to the primary prosthetic heart valve so that secondary prosthetic leaflets of the secondary prosthetic heart valve are positioned radially inward of the primary prosthetic leaflets of the primary prosthetic heart valve; and/or
coupling the secondary prosthetic heart valve to the primary prosthetic heart valve includes clipping clips of the secondary prosthetic heart valve to the primary prosthetic heart valve; and/or
clipping clips of the secondary prosthetic heart valve to the primary prosthetic heart valve includes clipping the clips to an atrial end the primary inner frame; and/or
clipping clips of the secondary prosthetic heart valve to the primary prosthetic heart valve includes clipping the clips to a ventricular end of the primary outer frame; and/or
the clips are configured to be actuated independently; and/or
the clips are configured to be actuated simultaneously; and/or
expanding the primary leaflets with a balloon expansion device prior to coupling the secondary prosthetic heart valve to the primary prosthetic heart valve; and/or
the primary inner frame is plastically expandable.

According to a third aspect of the disclosure, a balloon expansion device for expanding a portion of a prosthetic heart valve comprises:
a delivery catheter having a distal end extending along a center longitudinal axis; and
a plurality of balloons at least partially received within the delivery catheter, each of the plurality of balloons having a distal tip portion, a proximal portion, and a guidewire lumen extending to the distal tip portion for receiving a guidewire slidably therethrough, each of the guidewire lumens being radially offset from the center longitudinal axis of the delivery catheter, wherein the plurality of balloons is configured to be operably coupled to an expansion medium such that a volume of the expansion medium can be communicated to the plurality of balloons to expand the plurality of balloons; and/or each of the plurality of balloons has a middle portion between the proximal portion and the distal tip portion, the distal tip portion being narrower than the middle portion; and/or the proximal portion of each of the plurality of balloons has an enlarged diameter compared to a diameter of the middle portion; and/or the plurality of balloons includes three balloons arranged circumferentially around the center longitudinal axis of the delivery catheter; and/or each of the plurality of balloons is round or circular in cross-section.

According to a fourth aspect of the disclosure, a balloon expansion device for expanding a portion of a prosthetic heart valve comprises:

a delivery catheter; and
a single balloon at least partially received within the delivery catheter, the balloon having a distal tip portion, a proximal portion, a center portion between the proximal portion and the distal portion, and a guidewire lumen extending within the distal tip portion for receiving a guidewire slidably therethrough, the guidewire lumen and the distal tip portion being radially offset from a longitudinal centerline of the center portion of the balloon,
wherein the balloon is configured to be operably coupled to an expansion medium such that a volume of the expansion medium can be communicated to the balloon to expand the balloon; and/or
the balloon has a round or circular cross-section; and/or
the distal tip portion is narrower than the center portion of the balloon.

According to a fifth aspect of the disclosure, a prosthetic heart valve comprises:
a collapsible and expandable frame including an inner frame and an outer frame positioned radially outward of the inner frame;
a plurality of prosthetic leaflets coupled to the inner frame;
a tether having a first end configured to couple to the collapsible and expandable frame, and a second end opposite the first end; and
an anchor member coupled to the second end of the tether, wherein the tether includes a tether lumen extending therethrough, and a microcatheter positioned within the tether lumen, the microcatheter including a microcatheter lumen extending therethrough, the microcatheter being more rigid than the tether; and/or
the inner frame includes a tether connection portion defining a connection lumen configured to receive the tether therethrough so that the inner frame is slideable about the tether; and/or
a second anchor member coupled to the tether, the second anchor member being positioned between the anchor member and the first end of the tether; and/or
the anchor member is expandable; and/or
the second anchor member is non-expandable; and/or
the microcatheter includes a distal microcatheter tip protruding beyond the second end of the tether and beyond the anchor member.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of implanting a secondary prosthetic heart valve, the method comprising:
   delivering the secondary prosthetic heart valve to a vicinity of a native valve annulus, the native valve annulus having a primary prosthetic heart valve implanted therein, the primary prosthetic heart valve including a primary frame and a set of primary prosthetic leaflets, the secondary prosthetic heart valve being received within a delivery device in a collapsed condition during the delivering;
   releasing the secondary prosthetic heart valve from the delivery device to allow the secondary prosthetic heart valve to transition to an expanded condition; and
   coupling the secondary prosthetic heart valve to the primary prosthetic heart valve so that secondary prosthetic leaflets of the secondary prosthetic heart valve are positioned offset in relation to the primary prosthetic leaflets of the primary prosthetic heart valve, such that the secondary prosthetic leaflets are positioned a spaced distance from the primary prosthetic leaflets in a direction of blood flow through the primary prosthetic heart valve,
   wherein after coupling the secondary prosthetic heart valve to the primary prosthetic heart valve, the secondary prosthetic leaflets are positioned in series with the primary prosthetic leaflets so that the primary prosthetic leaflets are still free to move.

2. The method of claim 1, wherein the primary prosthetic heart valve is a prosthetic mitral valve or a prosthetic tricuspid valve, and the secondary prosthetic heart valve is positioned on an atrial side of the primary prosthetic heart valve in an upstream direction of blood flow through the primary prosthetic heart valve.

3. The method of claim 2, wherein the primary frame includes a primary inner frame to which the primary prosthetic leaflets are coupled, and a primary outer frame engaged with the native valve annulus.

4. The method of claim 3, wherein coupling the secondary prosthetic heart valve to the primary prosthetic heart valve includes engaging barbs, hooks, or anchors of the secondary prosthetic heart valve to the primary inner frame.

5. The method of claim 3, wherein coupling the secondary prosthetic heart valve to the primary prosthetic heart valve includes engaging barbs, hooks, or anchors of the secondary prosthetic heart valve to the primary outer frame.

6. The method of claim 3, wherein coupling the secondary prosthetic heart valve to the primary prosthetic heart valve includes engaging barbs, hooks, or anchors of the secondary prosthetic heart valve to a covering extending between the primary inner frame and the primary outer frame.

7. The method of claim 1, further comprising expanding the primary leaflets with a balloon expansion device prior to coupling the secondary prosthetic heart valve to the primary prosthetic heart valve.

8. A method of implanting a secondary prosthetic heart valve in a heart of a patient, the method comprising:
   delivering the secondary prosthetic heart valve to a vicinity of a native valve annulus, the native valve annulus having a primary prosthetic heart valve implanted therein, the primary prosthetic heart valve including a primary outer frame engaged to the native valve annulus, a primary inner frame, a set of primary prosthetic leaflets coupled to the primary inner frame, and a tether having a first end coupled to the primary inner frame and a second end coupled to an anchor that is engaged to a surface of the heart, the secondary prosthetic heart valve being received within a delivery device in a collapsed condition during the delivering;

releasing the secondary prosthetic heart valve from the delivery device to allow the secondary prosthetic heart valve to transition to an expanded condition; and coupling the secondary prosthetic heart valve to the primary prosthetic heart valve so that secondary prosthetic leaflets of the secondary prosthetic heart valve are positioned radially inward of the primary prosthetic leaflets of the primary prosthetic heart valve, wherein the secondary prosthetic heart valve is not introduced into the patient until after the primary prosthetic heart valve has begun to fail.

9. The method of claim 8, wherein coupling the secondary prosthetic heart valve to the primary prosthetic heart valve includes clipping clips of the secondary prosthetic heart valve to the primary prosthetic heart valve.

10. The method of claim 9, wherein clipping clips of the secondary prosthetic heart valve to the primary prosthetic heart valve includes clipping the clips to an atrial end the primary inner frame.

11. The method of claim 9, wherein clipping clips of the secondary prosthetic heart valve to the primary prosthetic heart valve includes clipping the clips to a ventricular end of the primary outer frame.

12. The method of claim 9, wherein the clips are configured to be actuated independently of each other.

13. The method of claim 9, wherein the clips are configured to be actuated simultaneously with each other.

14. The method of claim 8, further comprising expanding the primary leaflets with a balloon expansion device prior to coupling the secondary prosthetic heart valve to the primary prosthetic heart valve.

15. The method of claim 14, wherein the primary inner frame is plastically expandable.

16. The method of claim 14, wherein the primary inner frame is self-expandable.

* * * * *